United States Patent [19]
Greve et al.

[11] Patent Number: 6,143,298
[45] Date of Patent: Nov. 7, 2000

[54] SOLUBLE TRUNCATED FORMS OF ICAM-1

[75] Inventors: Jeffrey M. Greve, Woodbridge; Alan McClelland, Old Saybrook; Gary Davis, Milford, all of Conn.

[73] Assignee: Bayer Corporation, Pittsburgh, Pa.

[21] Appl. No.: 08/435,568

[22] Filed: May 5, 1995

Related U.S. Application Data

[62] Division of application No. 08/316,386, Sep. 30, 1994, which is a continuation of application No. 08/103,610, Aug. 6, 1993, abandoned, which is a continuation of application No. 07/704,996, May 24, 1991, abandoned, which is a continuation-in-part of application No. 07/631,313, Dec. 20, 1990, abandoned, which is a continuation-in-part of application No. 07/556,238, Jul. 20, 1990, abandoned, and a continuation-in-part of application No. 07/390,662, Aug. 10, 1989, abandoned, which is a continuation-in-part of application No. 07/239,571, Sep. 1, 1988, abandoned, and a continuation-in-part of application No. 07/262,428, Oct. 25, 1988, abandoned, which is a continuation-in-part of application No. 07/239,571, Sep. 1, 1988, abandoned.

[51] Int. Cl.[7] .......................... A61K 38/17; C07K 14/705
[52] U.S. Cl. ...................... 424/185.1; 530/300; 530/350; 530/395; 435/69.1; 435/69.3
[58] Field of Search .................................. 435/7.1, 69.3, 435/69.1; 530/350, 395, 300; 424/185.1

[56] References Cited

U.S. PATENT DOCUMENTS

| | | | |
|---|---|---|---|
| 4,171,365 | 10/1979 | Diana et al. | 424/273 |
| 4,209,526 | 6/1980 | Diana et al. | 424/273 |
| 4,232,161 | 11/1980 | Diana et al. | 546/279 |
| 4,234,725 | 11/1980 | Diana et al. | 544/140 |
| 4,261,928 | 4/1981 | Diana et al. | 568/331 |
| 4,372,976 | 2/1983 | Diana | 424/331 |
| 4,427,653 | 1/1984 | Springer | 424/85 |
| 4,451,476 | 5/1984 | Diana | 424/272 |
| 4,843,087 | 6/1989 | Diana | 514/374 |
| 4,956,281 | 9/1990 | Wallner et al. | 435/69.3 |
| 5,081,228 | 1/1992 | Dower et al. | 530/35.1 |
| 5,109,123 | 4/1992 | Reinherz et al. | 536/27 |
| 5,179,017 | 1/1993 | Axel et al. | |
| 5,235,049 | 8/1993 | McClelland et al. | 435/240.2 |
| 5,240,694 | 8/1993 | Gwaltney, Jr. | |
| 5,284,931 | 2/1994 | Springer et al. | 424/85.8 |
| 5,304,636 | 4/1994 | Blaas et al. | 530/350 |
| 5,324,510 | 6/1994 | Wegner et al. | |
| 5,340,800 | 8/1994 | Liu et al. | |
| 5,349,053 | 9/1994 | Landolfi | |

(List continued on next page.)

FOREIGN PATENT DOCUMENTS

| | | | |
|---|---|---|---|
| 14630/88 | 10/1988 | Australia | C07K 15/12 |
| 1551888 | 11/1988 | Australia | C07K 13/00 |
| 2633288 | 5/1989 | Australia | C12N 5/00 |
| 623105 | 6/1989 | Australia | C12N 5/02 |
| B-48767/90 | 2/1990 | Australia | C07K 13/00 |
| 637324 | 3/1990 | Australia | C07K 13/00 |
| 5129990 | 9/1990 | Australia | C07K 13/00 |
| 623105 | 5/1992 | Australia | C12N 5/02 |
| 637324 | 5/1993 | Australia | C07K 13/00 |
| 641134 | 9/1993 | Australia | C07K 13/00 |
| 652567 | 9/1994 | Australia | C07K 13/00 |
| 675441 | 2/1997 | Australia | C07K 15/06 |
| 1339193 | 8/1997 | Canada | A61K 38/17 |
| 0169146A3 | 1/1986 | European Pat. Off. | C12N 15/00 |
| 0192175A2 | 8/1986 | European Pat. Off. | C12N 5/00 |
| 0207453A2 | 1/1987 | European Pat. Off. | C07D 413/12 |
| 0227604A2 | 7/1987 | European Pat. Off. | C07K 7/08 |
| 0261403A2 | 3/1988 | European Pat. Off. | C12N 15/00 |
| 0280578A2 | 8/1988 | European Pat. Off. | C07K 3/20 |
| 0287076 | 10/1988 | European Pat. Off. | C12P 21/00 |

(List continued on next page.)

OTHER PUBLICATIONS

Smilek, D et al., PNAS 88:9633–37, A single amino acid change in myelin basic protein peptpdie confers the capacity to prevent rather than induce experimental autoimmune encephalomyelitis, Nov. 1991.

Abraham, G. and Colonno, R. J., "Many Rhinovirus Serotypes Share the Same Cellular Receptor", J. Virol. 51:340–345 (1984).

Anasetti et al., "Activation of Natural Killer Cells by LFA–3 Binding to CD2", Publication, Fred Hutchinson Cancer Research Center, Seattle WA, and Molecular Diagnostics, West Haven, CT (U.S.A.).

Argenbright et al., "Monoclonal Antibodies to the Leukocyte Membrane CD18 Glycoprotein Complex and to Intercellular Adhesion Molecule–1 Inhibit Leukocyte–Endothelial Adhesion in Rabbits", J. Leukoc. Biol. 49:253–257 (1991).

Argenbright, L. W. and Barton, R. W., "Interactions of Leukocyte Integrins with Intercellular Adhesion Molecule–1 in the Production of Inflammatory Vascular Injury In Vivo: the Shwartzman Reaction Revisited", J. Clin. Invest. 89(1):259–272 (1992).

Badger et al., "Structure Analysis of a Series of Antiviral Agents Complexed with Human Rhinovirus 14", PNAS 85:3304–3308 (1988).

Bangham, C. R. M. and McMichael, A. J., "Nosing ahead in the cold war" Nature 334:16 (1990).

Bebbington, C. R., and Hentschel, C. C. G. "The use of vectors based on gene amplification for the expression of cloned genes in mammalian cells" DNA Cloning 3:163–186 (1987).

Blann, A. D., "Cell Hybrids: an important new source of antibody production" Med. Lab. Sci. 36:329–338 (1979).

Bock et al., "Characterization of soluble forms of NCAM", FEBS Lett 225(1,2):33–36 (1987).

Bowie et al., "Deciphering the Message in Protein Sequences: Tolerance to Amino Acid Substitutions", Science 247:1306–1310 (1990).

Campbell, B. A. and Cords, C. E., "Monoclonal Antibodies That Inhibit Attachment of Group B Coxsackieviruses", J. Virol. 48(2):561–564 (1983).

Capon et al., "Designing CD4 immunoadhesins for AIDS therapy", Nature 337:525–531 (1989).

(List continued on next page.)

*Primary Examiner*—Thomas M. Cunningham

[57] ABSTRACT

Novel analogs of ICAM-1 and methods of using same for reducing human rhinovirus infection.

12 Claims, 11 Drawing Sheets

U.S. PATENT DOCUMENTS

| | | |
|---|---|---|
| 5,359,046 | 10/1994 | Capon et al. . |
| 5,372,933 | 12/1994 | Zamarron et al. . |
| 5,395,929 | 3/1995 | Corbi et al. . |
| 5,422,097 | 6/1995 | Gwaltney . |
| 5,472,849 | 12/1995 | Rothlein et al. ................ 435/7.94 |
| 5,475,091 | 12/1995 | Springer et al. . |
| 5,525,487 | 6/1996 | Gallatin et al. . |
| 5,532,127 | 7/1996 | Gallatin et al. . |
| 5,580,969 | 12/1996 | Hoke et al. . |
| 5,589,453 | 12/1996 | Greve . |
| 5,597,567 | 1/1997 | Whitcup et al. ................ 424/143.1 |
| 5,603,932 | 2/1997 | Blaas et al. .................... 424/184.1 |
| 5,612,216 | 3/1997 | Springer et al. . |
| 5,663,293 | 9/1997 | Gallatin et al. . |
| 5,674,982 | 10/1997 | Greve et al. . |
| 5,686,581 | 11/1997 | Greve et al. ................... 530/402 |
| 5,686,582 | 11/1997 | Greve et al. . |
| 5,712,245 | 1/1998 | Blaas et al. .................... 514/2 |
| 5,730,983 | 3/1998 | Wegner et al. ................. 424/185.1 |
| 5,821,341 | 10/1998 | McClelland et al. ........... 530/388.2 |
| 5,831,036 | 11/1998 | Springer et al. ............... 530/395 |
| 5,849,699 | 12/1998 | McClelland et al. ........... 514/12 |
| 5,871,733 | 2/1999 | Greve et al. ................... 424/134.1 |

FOREIGN PATENT DOCUMENTS

| | | | |
|---|---|---|---|
| 0287076B1 | 10/1988 | European Pat. Off. | ......... C12P 21/00 |
| 0289949A2 | 11/1988 | European Pat. Off. | ......... C12N 15/00 |
| 0314863A2 | 5/1989 | European Pat. Off. | ....... A61K 37/02 |
| 0319815A2 | 6/1989 | European Pat. Off. | ........... C12N 5/00 |
| 0380068A1 | 1/1990 | European Pat. Off. | ......... C12N 15/85 |
| 0362526A2 | 4/1990 | European Pat. Off. | ......... C12N 15/12 |
| 0362531A1 | 4/1990 | European Pat. Off. | ......... C07K 13/00 |
| 0364690A2 | 4/1990 | European Pat. Off. | ......... C07K 15/00 |
| 0365837A2 | 5/1990 | European Pat. Off. | ......... A61K 37/02 |
| 0379904A1 | 8/1990 | European Pat. Off. | ......... C07K 13/00 |
| 0387668A1 | 9/1990 | European Pat. Off. | ......... C12N 15/12 |
| 0387701B1 | 9/1990 | European Pat. Off. | ....... A61K 37/02 |
| 0391088A2 | 10/1990 | European Pat. Off. | ....... A61K 37/02 |
| 0459577A2 | 12/1991 | European Pat. Off. | ......... C07K 15/28 |
| 0468257 | 1/1992 | European Pat. Off. | ......... C12N 15/12 |
| 0510483 | 10/1992 | European Pat. Off. | ..... G01N 33/569 |
| 0566554 | 10/1993 | European Pat. Off. | ......... C12N 15/85 |
| 0319815 | 8/1994 | European Pat. Off. | ........... C12N 5/10 |
| 0169729A2 | 1/1996 | European Pat. Off. | ..... G01N 33/577 |
| 0379904 | 5/1996 | European Pat. Off. | ......... C12N 15/12 |
| 0488061 | 11/1998 | European Pat. Off. | ...... C07K 14/705 |
| 100601 | 1/1998 | Finland | ............... C12N 5/10 |
| 3712678A1 | 10/1988 | Germany | ........... C12N 5/00 |
| 74144 | 7/1997 | Ireland | ............. C12N 15/12 |
| 91454 | 8/1995 | Israel . | |
| 230474 | 8/1989 | New Zealand . | |
| 232203 | 1/1990 | New Zealand . | |
| 92920 | 7/1990 | Portugal | ........................ C07K 14/95 |
| 91570 | 11/1994 | Portugal . | |
| 202435 | 6/1999 | Rep. of Korea . | |
| 900469 | 10/1990 | South Africa . | |
| 52785 | 3/1992 | Taiwan | ........................... A61K 37/02 |
| 2022826 | 12/1979 | United Kingdom | ............ G01N 33/16 |
| WO 88/06592 | 9/1988 | WIPO | ............................. C07H 21/04 |
| WO 89/10938 | 11/1989 | WIPO | ............................. C07K 9/00 |
| WO 90/03400 | 4/1990 | WIPO | ............................. C07K 15/14 |
| WO 90/10646 | 9/1990 | WIPO | ............................. C07K 13/00 |
| WO 90/10652 | 9/1990 | WIPO | ............................. C07K 15/14 |
| WO 90/13316 | 11/1990 | WIPO | ........................... A61K 39/395 |
| WO 91/16927 | 11/1991 | WIPO | ........................... A61K 39/395 |
| WO 91/16928 | 11/1991 | WIPO | ........................... A61K 39/395 |
| WO 91/18010 | 11/1991 | WIPO | ............................. C07K 5/06 |
| WO 91/18011 | 11/1991 | WIPO | ............................. C07K 5/08 |
| 9201049 | 1/1992 | WIPO | ............................. C12N 15/00 |
| 9206119 | 4/1992 | WIPO | ............................. C07K 15/28 |
| 9212994 | 8/1992 | WIPO | ............................... C07K 3/06 |
| 9306842 | 4/1993 | WIPO | ............................. A61K 37/02 |
| 9306850 | 4/1993 | WIPO | ............................. A61K 37/02 |
| 9313210 | 8/1993 | WIPO | ............................. C12N 15/62 |
| 9401553 | 1/1994 | WIPO | ............................. C12N 15/12 |
| 9411400 | 5/1994 | WIPO | ............................. C07K 13/00 |
| 9527736 | 10/1995 | WIPO | ............................. C07K 16/28 |
| 9528170 | 10/1995 | WIPO | ............................. A61K 38/04 |
| 9606622 | 3/1996 | WIPO | ........................... A61K 31/715 |
| 9627292 | 9/1996 | WIPO | ............................. A01N 63/00 |
| 9634015 | 10/1996 | WIPO | ............................. C07K 16/28 |

OTHER PUBLICATIONS

Cate et al., "Isolation of the Bovine and Human Genes for Müllerian Inhibiting Substance and Expression of the Human Gene in Animal Cells", Cell 45:685–698 (1986).

Cole et al., "Topographic Localization of the Heparin–binding Domain of the Neural Cell Adhesion Molecule N–CAM", J. Cell Biol. 103:1739–1744 (1986).

Colonno et al., "Isolation of a Monoclonal Antibody that Blocks Attachment of the Major Group of Human Rhinoviruses", J. Virology 57:7–12 (1986).

Colonno, R. J. and Tomassini, J. E., "Viral Receptors: A Novel Approach For The Prevention Of Human Rhinovirus Infection", in *Medical Virology VI,* de la Maza, L. M. and E. M. Peterson, eds. (Elsevier, New York, 1987) 331–351.

Cooper, G.M., "Cellular Transforming Genes", Science 217: 801–806 (1982).

Couch, R.B., "Rhinoviruses", *Virology,* Second Edition, edited by B. N. Fields, D. M. Knipe et al. Raven Press, Ltd., New York, 607–629 (1990).

Couch et al., "Effect of Route Inoculation on Experimental Respiratory Viral Disease in Volunteers and Evidence for Airborne Transmission", Bacteriol. Rev. 30:517–529 (1966).

Creighton, T.E., *Proteins* by W. H. Freeman and Company, New York, 33–34 (1984).

Crump et al., "In Vitro Inhibitory Activity of Soluble ICAM–1 for the Numbered Serotypes of Human Rhinovirus", Antiviral Chemistry and Chemother. 4(6):323–327 (1993).

Cunningham et al., "Neural Cell Adhesion Molecule: Structure, Immunoglobulin–Like Domains, Cell Surface Modulation, and Alternative RNA Splicing", Science 236:799–806 (1987).

Cybulsky, M. I. and Gimbrone, Jr., M. A., "Endothelial Expression of a Mononuclear Leukocyte Adhesion Molecule During Atherogenesis", Science 251:788–791 (1991).

D'Alessio et al., "Short–Duration Exposure and the Transmission of Rhinoviral Colds", J. Inf. Dis. 150(2):189–193 (1984).

Deen et al., "A Soluble Form of CD4 (T4) Protein Inhibits AIDS Virus Infection", Nature 331:82–86 (1988).

Dick, E.C., "Experimental Infection of Chimpanzees with Human Rhinovirus Types 14 and 43", Proceedings Of The Society For Experimental Biology And Medicine 127:1079–1081 (1968).

Dochez et al., "Studies in the Common Cold. IV. Experimental Transmission of the Common Cold to Anthropoid Apes and Human Beings by Means of a Filtrable Agent", J. Exp. Med. 52:701–716 (1930).

Douglas et al., "Prophylactic Efficacy of Intranasal Alpha 2–Interferon Against Rhinovirus Infections in the Family Setting", The New England J. of Med. 314:65–70 (1986).

Douglas, R. G., "Pathogenesis of Rhinovirus Common Colds in Human Volunteers", Annals of Otology, Rhinology and Laryngology 79:563–571 (1970).

Dustin et al., "Induction by IL 1 and Interferon–γ: Tissue Distribution, Biochemistry, and Function of a Natural Adherence Molecule (ICAM–1)", J. Immunol. 137(1):245–254 (1986).

Dustin et al., "Supergene Families Meet in the Immune System" Immunology Today, 9(7 and 8):213–215 (1988).

Dustin et al., "Correlation of CD2 Binding and Functional Properties of Multimeric and Monomeric Lymphocyte Function–Associated Antigen 3", J. Exp. Med. 169:503–517 (1989).

Ey, P.L., et al., "Isolation of Pure IgG1, IgG2a, and IgG2b Immunoglobulins from Mouse Serum Using Protein A—Sepharose", Immunochemistry 15:429–436 (1978).

Fisher et al., "HIV Infection is Blocked in vitro by Recombinant Soluble CD4", Nature 331:76–78 (1988).

Fox et al., "Prevention of a Rhinovirus and Poliovirus Uncoating by WIN 51711, a New Antiviral Drug", Antimicrob. Ag. and Chemotherapy 30:110–116 (1986).

Galfrey et. al., "Antibodies to Major Histocompatibility Antigens Produced by Hybrid Cell Lines", Nature 266:550–552 (1977).

Gething, M.J. and Sambrook, J., "Construction of Influenza Haemagglutinin Genes that Code for Intracellular and Secreted Forms of the Protein" Nature 300:598–603 (1982).

Ginsberg et al., "Inhibition of Fibronectin Binding to Platelets by Proteolytic Fragments and Synthetic Peptides Which Support Fibroblast Adhesion", J. Biol. Chem. 260(7): 3931–3936 (1985).

Giranda et al., "Modeling of the Human Intercellular Adhesion Molecule–1, the Human Rhinovirus Major Group Receptor" Proteins: Structure, Function, and Genetics, 7:227–233 (1990).

Gough, N., "Putting A Stop To An Immunoglobulin Message", Trends Genet. 3(9):238–240 (1987).

Gower et al., "Alternative Splicing Generates a Secreted Form of N–CAM in Muscle and Brain", Cell 55:955–964 (1988).

Graham, F.L., and Van der Eb, A. J., "A New Technique for the Assay of Infectivity of Human Adenovirus 5 DNA", Virology 52: 456–467 (1973).

Green et al., "Immunogenic Structure of the Influenza Virus Hemagglutinin", Cell 28:477–487 (1982).

Greve et al., "The Major Human Rhinovirus Receptor Is ICAM–1", Cell 56:839–847 (1989).

Greve et al., "Mechanisms of Receptor–Mediated Rhinovirus Neutralization Defined by Two Soluble Forms of ICAM–1", J. Virology 65:6015–6023 (1991).

Gross–Bellard et al., "Isolation of High–Molecular–Weight DNA from Mammalian Cells", Eur. J. Biochem. 36:32–38 (1973).

Güssow, D. and Ploegh, H., "Soluble class I antigens: a conundrum with no solution?", Immunology Today 8(7, 8):220–222 (1987).

Gwaltney et al., *Diagnostic Procedures for Viral, Rickettsial and Chlamydial Infections,* N. J. Schmidt and R. W. Evans, Eds, 6th edition. pp. 603, Am Pub. Health. Assoc., Washington D.C. (1989).

Halperin et al., "Exacerbations of Asthma in Adults During Experimental Rhinovirus Infection", Am. Rev. Respir. Dis. 132:976–980 (1985).

Hamparian et al., "A Collaborative Report: Rhinoviruses–Extension of the Numbering System from 89 to 100", Virology 159:191–192 (1987).

Hardy et al., "Intranasal Drug Delivery by Spray and Drops", J. Pharm. Pharmacol. 37:294–297 (1985).

Harning et al., "Serum Levels of Circulating Intercellular Adhesion Molecule 1 in Human Malignant Melanoma", Cancer Res. 51(8):5003–5005 (1991).

Hayden et al., "Safety and Efficacy of Intranasal Pirodavir (R77975) in Experimental Rhinovirus Infection", Antimicrob. Agents Chemother. 36(4):727–732 (1992).

Hayden et al., "Prevention of Natural Colds by Contact Prophylaxis with Intranasal Alpha2–Interferon", The New England Journal of Medicine, 314(2):71–75 (1986).

Hayden et al., "Modification of Experimental Rhinovirus Colds by Receptor Blockade" Antiviral Research 9:233–247 (1988).

Helenius, A. and Von Bonsdorff, C. H., "Semliki Forest Virus Membrane Proteins, Preparation and Characterization of Spike Complexes Soluble in Detergent–Free Medium" Biochimica et Biophysica Acta 436:895–899 (1976).

Hendley et al., "Relation Between Naturally acquired Immunity and Infectivity of Two Rhinoviruses in Volunteers", J. Inf. Dis. 125:243–248 (1972).

Holland, J. J. and McLaren, L. C., "The mammalian cell–virus relationship. II. Absorption, Reception and Eclipse of Poliovirus by HeLa Cells" J. Exp. Med. 109:487–504 (1959).

Holland, J. J., "Receptor affinities as Major Determinants of Enterovirus Tissue Tropisms in Humans", Virology 15:312–326.

Horton et al., "Gene Splicing by Overlap Extension: Tailor–Made Genes Using the Polyerase Chain Reaction", BioTechniques 8(5):528–535 (1990).

Hussey et. al., "A Soluble CD4 Protein Selectively Inhibits HIV Replication and Syncytium Formation" Nature, 331:78–81 (1988).

Illum, L., "The Nasal Delivery of Peptides and Proteins", Trends in Biotech. 9:284–289 (1991).

Johnston et al., "Viruses as Precipitants of Asthma Symptoms. III. Rhinoviruses: Molecular Biology and Prospects for Future Intervention", Clin. Exp. Allergy, 23:237 (1993).

Johnston et al., "Viral Infections in Exacerbations in School Children with Cough or Wheeze: A Longitudinal Study", Am. Rev. Resp. Dis., 145:A546 (1992).

Kamarck, M. E., and Ruddle, F. H., "Somatic Cell Genetics and the Human Gene Map", Chapter 105 in *Handbook of Experimental Immunology in Four Volumes, vol. 3: Genetics and Molecular Immunology,* D. M. Weir, ed. (Blackwell Scientific Publications, Boston, MA, 1986).

Katz et al., "Chromosome Mapping of Cell Membrane Antigens Expressed on Activated B Cells", Eur. J. Immunol., 15:103–106 (1985).

Kavenoff, R., and Zimm, B. H., "Chromosome–Sized DNA Molecules from Drosophila", Chromosoma (Berl.) 41:1–27 (1973).

Kühn et al., "Gene Transfer, Expression, and Molecular Cloning of the Human Transferrin Receptor Gene", Cell 37:95–103 (1984).

Lebman et al., "A Monoclonal Antibody that Detects Expression of Transferrin Receptor in Human Erythroid Precursor Cells", Blood 59(3):671–678 (1982).

Lemanske et al., "Rhinovirus Upper Respiratory Infection Increases Airway Hyperreactivity and Late Asthmatic Reactions", J. Clin. Invest. 83:1–10 (1989).

Littlefield, J.W., "Selection of Hybrids from Matings of Fibroblasts in vitro and Their Presumed Recombinants", Science 145:709–710 (1964).

Lonberg–Holm et al., "Unrelated Animal Viruses Share Receptors", Nature 259:679–681 (1976).

Margulies, D. H., et al., "Engineering Soluble Major Histocompatibility Molecules: Why and How", Immunol. Res. 6: 101–116 (1987).

Marlin, S.D. and Springer, T. A., "Purified Intercellular Adhesion Molecule–1 (ICAM–1) Is a Ligand for Lymphocyte Function–Associated Antigen 1 (LFA–1)", Cell 51:813–819 (1987).

Marlin et al., "A Soluble Form of Intercellular Adhesion Molecule–1 Inhibits Rhinovirus Infection", Nature 344:70–72 (1990).

Marsh et al., "Antibody–toxin Conjugation", *Immunotoxins* by Kluwer Academic Publishers, Boston, Dordrecht, Lancaster 213–237 (1988).

Marsh et al., "Interactions of Semliki Forest Virus Spike Glycoprotein Rosettes and Vesicle with Cultures Cells", J. Cell Biology 96:455–461 (1983).

McClelland et al., "Identification of Monoclonal Antibody Epitopes and Critical Residues for Rhinovirus in Domain 1 of ICAM–1", PNAS 88(18):7993–7997 (1991).

McClelland et al., "Transfectant cell lines which express the major human rhinovirus receptor, their preparation, and their uses", Chemical Abstracts 112:117175h (1990).

McCray, J. and Werner, G., "Different Rhinovirus Serotypes Neutralized by Antipeptide Antibodies", Nature 329:736–738 (1987).

Medical Microbiology: "An Introduction to Infectious Diseases", 2nd ed., J.C. Sherris, ed. (Elsevier Science Publishing Co., Inc., N.Y. 1990) pp 514–515.

Medrano, L. and Green, H., "Picornavirus Receptors and Picornavirus Multiplication in Human–Mouse Hybrid Cell Lines", Virology 54:515–524 (1973).

Melchers et al., *Lymphocyte Hybridomas,* vol. 81 of Current Topics in Microbiology and Immunology, W. Arber, W. Henle, P.H. Hofschneider, J.H. Humphrey, J. Klein, P. Koldovsky, H. Koprowski, O. Maaloe, F. Melchers, R. Rott, H.G. Schweiger, L. Syrucek, P.K. Vogt, eds (Springer Verlang, New York, 1978).

Mendelsohn et al., "Transformation of a Human Poliovirus Receptor Gene into Mouse Cells", PNAS 83:7845–7849 (1986).

Minor, P.D., "Growth, Assay and Purification of Picornaviruses", in *Virology: A Practical Approach,* B.W.J. Mahy, ed. (IRL Press Limited, Oxford, England), 25–41 (1985).

Minor et al., "Monoclonal antibodies which block cellular receptors of poliovirus", Virus Research 1:203–212 (1984).

Morein, B., "Potentiation of the Immune Response by Immunization with Antigens in Defined Multimeric Physical Forms", Veterinary Immunology and Immunopathology 17:153–159 (1987).

Niman et al., "Anti–peptide antibodies detect oncogene–related proteins in urine", PNAS 82:7924–7928 (1985).

Nobis et al., "Production of a Monoclonal Antibody against an Epitope on HeLa Cells that Is the Functional Poliovirus Binding Site", J. Gen. Virol. 66:2563–2569 (1985).

Ohlin et al., "Spectrum of Activity of Soluble Intercellular Adhesion Molecule–1 Against Rhinovirus Reference Strains and Field Isolates", Antimicrob. Agents and Chemother. 38:1413–1415 (1994).

Parham, P., "Monoclonal Antibodies Against HLA Products and Their use in Immunaffinity Purification," Methods in Enzymology 92:110–138 (1983).

Pepinsky et al., "The Increased Potency of Crossed–linked Lymphocyte Function–associated Antigen–3 (LFA–3) Multimers Is a Direct Consequence of Changes in Valency", J. Biol. Chem. 266(27):18244–18249 (1991).

Peterson, A. and Seed, B., "Genetic Analysis of Monoclonal Antibody and HIV Binding Sites on the Human Lymophocyte Antigen CD4", Cell 54:65–72 (1988).

Rossman et al., "Structure of a Human Common Cold Virus and Functional Relationship to other Picornaviruses", Nature 317: 145–153 (1985).

Rothlein et al., "A Form of Circulating ICAM–1 In Human Serum", J. Immuno. 147(11):3788–3793 (1991).

Rothlein et al., "A Human Intercellular Adhesion Molecule (ICAM–1) Distinct From LFA–1", J. Immuno. 137(4):1270–1274 (1986).

Ruddle et al., "DNA–Mediated Gene Transfer in Mammalian Gene Cloning", Genetic Engineering 6:319–338 (1984).

Ruoslahti et al., "Synthetic Peptides in the Analysis of Cell Adhesion," in *Synthetic Peptides in Biology and Medicine* Elsevier Science Publishers, pp. 191–197 (1985).

Saiki et al., "Enzymatic Amplification of β–Globin Genomic Sequences and Restriction Site Analysis for Diagnosis of Sickle Cell Anemia," Science 230:1350–1354 (1985).

Sambrook et al., *Molecular Cloning: A Laboratory Manual,* 2d ed. (Cold Spring Harbor Laboratory Press, Cold Spring Harbor, NY, 1989) pp. 1.21–1.52.

Schipper et al., "The Nasal Mucocilliary Clearance: Relevance to Nasal Drug Delivery", Pharm. Res. 8:807–814 (1991).

Scopes, R.K., "Separation By Precipitation," in *Protein Purification: Principles & Practice* (1982) Springler Verlag, NY, pp. 39–46.

Seed, B. and Aruffo, A., "Molecular Cloning of the CD2 antigen, the T–Cell Erythrocyte Receptor, by a Rapid Immunoselection Procedure," PNAS 84:3365–3369 (1987).

Seed, B., "An LFA–3 cDNA Encodes a Phospholipid–Linked Membrane Protein Homologous to its Receptor CD2," Nature 329: 840–842 (1987).

Seth et al., "Circulating ICAM–1 isoforms: Diagnostic Prospects for Inflammatory and Immune Disorders," Lancet 338:83–84 (1991).

Sherman–Gold, R., "Companies Pursue Therapies Based on Complex Cell Adhesion Molecules", Genetic Engineering News pp. 6–7,14 (Jul. 1993).

Sherry, B. and Rueckert, R., "Evidence for at Least Two Dominant Neutralization Antigens on Human Rhinovirus 14," J. Virol. 53(1):137–143 (1985).

Shih, C. and Weinberg, R. A., "Isolation of a Transforming Sequence from a Human Bladder Carcinoma Cell Line," Cell 29: 161–169 (1982).

Shipkowitz et al., "Antiviral Activity of a bis–Benzimidazole Against Experimental Rhinovirus Infections in Chimpanzees", App. Microbiol. 23(1):117–122 (1972).

Siddique et al., "The Poliovirus Sensitivity (PVS) Gene Is on Chromosome 19q12–>q13.2", Genomics 3:156–160 (1988).

Simmons et al., "ICAM, an Adhesion Ligand of LFA–1, is Homologous to the Neural Cell Adhesion Molecule NCAM," Nature 331:624–627 (1988).

Simons et al., "Formation of Protein Micelles from Amphiphilic Membrane Proteins", PNAS 75(11):5306–5310 (1978).

Skerra, A. and Pluckthun, A., "Assembly of a Functional Immunoglobulin FV Fragment in *Escherichia Coli*" Science, 240: 1038–1041 (1988).

Smith, T.J., et al., "The Site of Attachment in Human Rhinovirus 14 for 4 Antiviral Agents that Inhibit Uncoating", Science 233:1286–1293 (1986).

Smith et al., "Blocking of HIV–1 Infectivity by a Soluble, Secreted Form of the CD4 Antigen," Science 238:1704–1707 (1987).

Smith et al., "Modification and Secretion of Human Interleukin 2 Produced in Insect Cells by a Baculovirus Expression Vector", PNAS 82:8404–8408 (1985).

Springer, T.A., "Adhesion Receptors of the Immune System", Nature 346:425–434 (1990).

Staunton et al., "Primary Structure of ICAM–1 Demonstrates Interaction between Members of the Immunoglobulin and Integrin Supergene Families," Cell 52:925–933 (1988).

Staunton et al., "The Arrangement of the Immunoglobulin––Like Domains of ICAM–1 and the Binding Sites for LFA–1 and Rhinovirus," Cell 61:243–254 (1990).

Staunton et al., "A Cell Adhesion Molecule, ICAM–1, is the Major Surface Receptor for Rhinoviruses," Cell 56:849–853 (1989).

Steis et al., "Serum Soluble IL–2 Receptor as a Tumor Marker in Patients with Hairy Cell Leukemia", Blood 71(5):1304–1309 (May 1988).

Sundquist et al., "Influenza Virus ISCOMs: Antibody Response in Animals", Vaccine 6:49–53 (1988).

Sundquist et al., "Influenza Virus ISCOMs: Biochemical Characterization", Vaccine 6:44–48 (1988).

Tomassini, J.E., "Isolation, Characterization and Cloning of the Cellular Receptor for the Major Group of Human Rhinoviruses," Ph.D. Thesis, University of Pennsylvania (1986).

Tomassini, J.E. and Colonno, R. J., "Isolation of a Receptor Protein Involved in Attachment of Human Rhinoviruses," J. Virol. 58(2):290–295 (1986).

Tomassini et al., "CDNA Cloning Reveals that the Major Group Rhinovirus Receptor on HeLa Cells is Intercellular Adhesion Molecule 1," PNAS 86:4907–4911 (1989).

Towbin et. al., "Electrophoretic Transfer of Proteins from Polyacrylamide Gels to Nitrocellulose Sheets: Procedure and Some Applications", PNAS 76(9):4350–4354 (1979).

Traunecker et al., "Highly Efficient Neutralization of HIV with Recombinant CD4–Immunoglobulin Molecules," Nature 339: 68–70 (1989).

Traunecker et al., "Soluble CD4 Molecules Neutralize Human Immunodeficiency Virus Type 1" Nature 331:84–86 (1988).

Turner et al., "Efficacy of Oral WIN 54954 for Prophylaxis of Experimental Rhinovirus Infection", 37:297–300 (1993).

Urlaub, G. and Chasin, L. A., "Isolation of Chinese Hamster Cell Mutants Deficient in Dihydrofolate Reductase Activity," PNAS USA 77(7):4216–4220 (1980).

Wade, N., "Hybridomas: A Potent New Biotechnology," Science 208:692–693 (1980).

Welsh, K.I., "Antibody Production Made Easier," Nature 266: 495 (1977).

Wigler et al., "Transformation of Mammalian Cells with Genes from Procaryotes and Eucaryotes," Cell 16:777–785 (1979).

Williams, A. F., "A Year in the Life of the Immunoglobulin Superfamily", Immunology Today 8(10):298–303 (1987).

Williams, A. F. and Barclay, A. N.,"The Immunoglobulin Superfamily–Domains for Cell Surface Recognition[1,2]", Ann. Rev. Immunol. 6:381–405 (1988).

Winther et al., "Sites of Rhinovirus Recovery After Point Inoculation of the Upper Airway", JAMA 256(13):1763–1767 (1986).

Woods et al., "In Vitro and In Vivo Activities of WIN 54954, a New Broad Spectrum Antipicornavirus Drug", Antimicrob. Agents Chemother 33:2069–2074 (1989).

Zettlmeissl et al., "Expression and Characterization of Human CD4: Immunoglobulin Fusion Proteins," DNA and Cell Biology 9: 347–353 (1990).

Braude, A. (ed.s), Infectious Diseases and Medical Microbiology, 2nd edition, W.B. Saunders Co., Philadelphia, PA, (1986) chapter 65 "Picornaviruses", pp. 521–529.

Gennaro, A.R. (ed.), Remington's Pharmaceutical Sciences, 18th edition, Mack Publishing Co., Easton, PA (1990), "Drug Absorption, Action and Disposition", pp. 707–721.

Martin et al., "Efficient Neutralization and Disruption of Rhinovirus by Chimeric ICAM–1/Immunoglobulin Molecules", J. Virology, 67(6):3561–3568 (Jun. 1993).

Hendley et al., "Transmission of Rhinovirus Colds By Self–Inoculation", The New England Journal of Medicine, 288(26):1361–1364 (Jun. 28, 1973).

Hendley, J. O., and Gwaltney, J. M., Jr., "Mechanisms of Transmission of Rhinovirus Infections", Epidemiologic Reviews, 10:242–257 (1988).

Suter, David, Associated Press, "Tests for a Nasal Spray to Deflect Cold Viruses", New York Times, Sep. 20, 1995.

Manning, Anita, "War on Bacteria Mix of Victories Amid Warnings", USA Today, Sep. 20, 1995.

Haney, Daniel Q., "Beyond Chicken Soup. Nasal Spray Keeps Chimps From Catching Cold Virus", St. Louis Post Dispatch, Sep. 20, 1995.

Associated Press, "Common Colds: Nasal Spray May Help Keep The Sniffles Away", Atlanta Constitution, Sep. 20, 1995.

Associated Press, "Drug Sprays Away Colds", New York Post, Sep. 20, 1995.

Haney, Daniel Q., Associated Press, "The Cold War: Scientists Develop Spray That May End Sniffles", Arizona Republic, Sep. 20, 1995.

Haney, Daniel Q., Associated Press, "For Colds, Nasal Spray Holds Hope. A Protein Swamps The Virus With Potential Targets In The Nose. Its a Decoy Trick", Philadelphia Inquirer, Sep. 20, 1995.

Associated Press, "Simple Nasal Spray May Be Able To Keep Common Cold Away. Medicine Successful On Chimps So Far", Washington Times, Sep. 20, 1995.

Associated Press, "Doctors Sniffing Out Spray to Fight Colds", Denver Post, Sep. 20, 1995.

Associated Press, "Someday Soon, A Simple Sniff Should Snuff The Sniffles", Houston Chronicle, Sep. 20, 1995.

Haney, Daniel Q., Associated Press, "Spray May Ward Off Sniffles. Nasal Treatment Studied To Keep Cold Viruses From Invading Victim", Denver–Rocky Mountain News, Sep. 20, 1995.

Haney, Daniel Q., Associated Press, "Scientists Make Headway In Cold War With Nose Spray", Chicago Sun–Times, Sep. 20, 1995.

Haney, Daniel Q., Associated Press, "Labs Busy Working On Nose Spray To Keep Colds Away", Charlotte Observer, Sep. 20, 1995.

Associated Press, "Nasal Spray May Prevent Sniffles", Miami Herald, Sep. 20, 1995.

Associated Press, "Cure For The Cold? No, But Prevention May Be Spray Away", San Diego Union–Tribune, Sep. 20, 1995.

Haney, Daniel Q., "Nasal Spray Touted As Next–Best Thing To Cure For Colds", The Montreal Gazette, Sep. 20, 1995.

Associated Press, "Scientists Feel They Can Develop Spray To Keep The Sniffles Away", The Spectator, Sep. 20, 1995.

Haney, Daniel Q., Associated Press, "New Nasal Spray May Take Sniffles Out Of Common Cold", Cleveland Plain Dealer, Sep. 20, 1995.

Associated Press, No Cure, But Nothing To Sniff(le) At. Nasal Spray To Block Common Cold Is In The Works, Minneapolis Star Tribune, Sep. 20, 1995.

Haney, Daniel Q., Associated Press, "Out Front: Progress On Cold Front. Spray May Ward Off Sniffles. Medicine Is First To Block Infection", Sep. 19, 1995.

Monitoring Report, "Cure For Colds 9/18 to 9/20", Video Monitoring Services of America, a Burrelle's Affiliate, New York, New York, pp. 1–3, Sep. 20, 1995.

Al–Nakib, W., P.G. Higgins, G.I. Barrow, D.A.J. Tyrrell, K. Andries, G. Vanden Bussche, N. Taylor, and P.A.J. Janssen, "Suppression of Colds in Human Volunteers Challenged with Rhinoviurs by a New Synthetic Drug (R61837)", Antimicrobial Agents and Chemotherapy 33(4): 522–525 (Apr. 1989).

Amzel, L. M., and R.J. Poljak, " Three–Dimensional Structure of Immunoglobulins", Ann. Rev. Biochem. 48: 961–997 (1979).

Becker, J. W., and G.N.Reeke, Jr., "Three–dimensional structure of $\beta_2$–microglobulin", Proc. Natl. Acad. Sci. USA 82: 4225–4229 (Jun. 1985).

Becker, J. W., H.P. Erickson, S. Hoffman, B.A. Cunningham, and G.M. Edelman, "Topology of cell adhesion molecules", Proc. Natl. Acad. Sci. USA, 86: 1088–1092 (Feb. 1989).

Bjorkman, P. J., M.A. Saper, B. Samraoui, W.S. Bennett, J.L. Strominger, and D.C. Wiley, "Structure of the human class I histocompatibility antigen, HLA–A2", Nature 329: 506–512 (Oct. 1987).

Colman, P. M., "Structure of Antibody–Antigen Complexes: Implications for Immune Recognition", Advances in Immunology 43: 99–132 (1988).

Colonno, R. J., J.H. Condra, S. Mizutani, P.L. Callahan, M.–E.Davies, and M.A. Murcko, "Evidence for the direct involvement of the rhinovirus canyon in receptor binding", Proc. Natl. Acad. Sci. USA 85: 5449–5453 (Aug. 1988).

Craig, A. G. and A.R. Berendt, "The Role of ICAM–1 as a Receptor for Rhinovirus and Malaria", in *Integrins and ICAM–1 in Immune Responses,* N. Hodd, ed.(Chem Immunol. Basel, Karger, 1991), vol. 50, pp. 116–134 (1991).

Crump, C. E., E. Arruda, and F.G. Hayden, "Comparative Antirhinoviral Activities of Soluble Intercellular Adhesion Molecule–1 (sICAM–1) and Chimeric ICAM–1/Immunoglobulin A Molecule", Antimicrobial Agents and Chemotherapy 38(6): 1425–1427 (Jun. 1994).

Dayhoff, M. O., W.C. Barker, and L.T. Hunt, "Establishing Homologies in Protein Sequences", Methods in Enzymology 91: 524–545 (1983).

Dearden, C., W. Al–Nakib, K. Andries, R. Woestenborghs, and D.A.J. Tyrrell, "Drug resistant rhinoviruses from the nose of experimentally treated volunteers", Arch. Virol. 109: 71–81 (1989).

Dustin, M. L. and T.A. Springer, "Lymphocyte Function–associated Antigen–1 (LFA–1) Interaction with Intercellular Adhesion Molecule–1 (ICAM–1) is One of At Least Three Mechanisms for Lymphocyte Adhesion to Cultured Endothelial Cells", J. Cell Biol. 107: 321–331 (Jul. 1988).

Ezekovitz, R.A.B., R.B. Sim, G.G. MacPherson, and S. Gordon, "Interaction of Human Monocytes, Macrophages, and Polymorphonuclear Leukocytes with Zymosan in Vitro: Role of Type 3 Compliment Receptors and Macrophage Derived Complement", J. Clin. Invest. 76: 2368–2376 (Dec. 1985).

Greve, J. M., C.P. Forte, C.W. Marlor, A.M. Meyer, H. Hoover–Litty, D. Wunderlich, and A. McClelland, "Mechanisms of Receptor–Mediated Rhinovirus Neutralization Defined by Two Soluble Forms of ICAM–1", J. Virol. 65(11): 6015–6023 (Nov. 1991).

Guttman, N., and D. Baltimore, "Plasma Membrane Component Able to Bind and Alter Virions of Poliovirus Type 1: Sutides on Cell–Free Alteration Using a Simplified Assay", Virol. 82: 25–36 (1977).

Gwaltney, J. M., Jr., and J.O. Hendley, "Rhinovirus Transmission: One if by Air, Two if by Hand", Trans. Am. Clin. Climatol. Assoc. 89: 194–200 (1977).

Gwaltney, J. M.,Jr., and J.O. Hendley, "Rhinovirus Transmission One if by Air, Two if by Hand", Am. J. Epid. 107(5): 357–361 (May 1978).

Gwaltney, J. M. , Jr., "Rhinovirus colds: epdimiology, clinical characteristics and transmission", Eur. J. Respir. Dis. 64 (suppl. 128): 336–339 (1983).

Gwaltney, J. M., Jr., "Rhinoviruses", Yale J. Biol. Med. 48: 17–45 (1975).

Hayden, F. G., and J.M. Gwaltney, Jr., "Intranasal Interferon–$\alpha_2$ Treatment of Experimental Rhinoviral Colds", J. Infect. Dis. 150(2): 174–180 (Aug. 1984).

Hendley, J. O., and J.M. Gwaltney, Jr., "Mechanisms of Transmission of Rhinovirus Infections", Epidemiologic Reviews 10: 242–258 (1988).

Horley, K. J., C. Carpenito, B. Baker, and F. Takei, "Molecular cloning of murine intercellular adhesion molecule (ICAM–1)", EMBO J. 8(10): 2889–2896 (1989).

Jacobs, K., C. Shoemaker, R. Rudersdorf, S.D. Neill, R.J. Kaufman, A. Mufson, J. Seehra, S.S. Jones, R. Hewick, E.F. Fritsch, M. Kawakita, T. Shimizu, and T. Miyake, "Isolation and characterization of genomic and cDNA clones of human erythropoietin", Nature 313: 806–810 (Feb. 1985).

Kim S., T.J. Smith, M.S. Chapman, M.G. Rossmann, D.C. Pevear, F.J. Dutko, P.J. Felock, G.D. Diana, and M.A. McKinlay, "Crystal Structure of Human Rhinovirus Serotype 1A (HRV1A)", J. Med. Biol. 210: 91–111 (1989).

Layne S.P., M.J. Merges, M. Dembo, J.L. Spouge, and P.L. Nara, "HIV requires multiple gp120 molecules for CD4–mediated infection", Nature 346: 277–279 (Jul. 1990).

Leonard, W.J., J.M. Depper, G.R. Crabtree, S. Rudikoff, J. Pumphrey, R.J. Robb, M. Krönke, P.B. Svetlik, N.J. Peffer, T.A. Waldmann, and W.C. Greene, "Molecular cloning and expression of cDNAs for the human interleukin–2 receptor", Nature 311: 626–631 (Oct. 1984).

Leszczynski, J. F., and G.D. Rose, "Loops in Globular Proteins: A Novel Category of Secondary Structure", Science 234: 849–855 (Nov. 1986).

Lineberger, D. W., D.J. Graham, J.E. Tomassini, and R.J. Colonno, "Antibodies that Block Rhinovirus Attachment Map to Domain 1 of the Major Group Receptor", J. Virol. 64(6): 2582–2587 (Jun. 1990).

Martin, S., J.M. Casanovas, D.E. Staunton, and T.A. Springer, "Erfolgreiche Blockade von Rhinovirusinfektionen durch ICAM–1–Immunoglobulinchimare in vitro", Med. Klin. 88(4): 193–197 (1993).

McPherson, J. M., and D.J. Livingston, "Protein Engineering: New Approaches to Improved Therapeutic Proteins, Part I", in *Biotech. Trends*, S. Petska, ed. (Pharmaceutical Technology, May 1989).

Livingston, D. J., and J.M. McPherson, "Protein Engineering: New Approaches to Improved Therapeutic Proteins, Part II", in *Biotech. Trends*, S. Petska, ed. (Pharmaceutical Technology, Jun. 1989).

McPherson, J. M., and D.J. Livingston, "Protein Engineering: New Approaches to Improved Therapeutic Proteins, Part III", in *Biotech. Trends*, S. Petska, ed. (Pharmaceutical Technology, Sep. 1989).

McClelland, A., M.E.Kamarck, and F.H. Ruddle, "Molecular Cloning of Receptor Genes by Transfection", Methods in Enzymology 147: 280–291 (1987).

Minor, P.D., "Chapter 2: Growth, Assay and Purification of Picornaviruses", in *Virology: a practical approach* (IRL Press, Washington, D.C., 1985), pp. 25–41.

Minor, P. D., P.A. Pipkin, D. Hockley, G.C. Schild, and J.W. Almond, "Monoclonal antibodies which block cellular receptors of poliovirus", Virus Res. 1: 203–212 (1984).

Morein B., "Potentiation of the Immune Response by Immunization with Antigens in Defined Multimeric Physical Forms", Vet. Immunol. Immunopathol. 17: 153–159 (1987).

Ockenhouse, C.F., R. Betageri, T.A. Springer, and D.E. Staunton, "Plasmodium falciparum–Infected Erythrocytes Bind ICAM–1 at a Site Distinct from LFA–1, Mac–1, and Human Rhinovirus", Cell 68:63–69 (Jan. 1992).

Peppel, K., D. Crawford, and B. Beutler,"A Tumor Necrosis Factor (TNF) Receptor–IgG Heavy Chain Chimeric Protein as a Bivalent Antagonist of TNF Activity", J. Exp. Med. 174: 1483–1489 (Dec. 1991).

Pevear, D. C., M.J. Fancher, P.J. Felock, M.g. Rossmann, M.S. Miller, G. Diana, A.M. Treasurywala, M.A. McKinlay, and F.J. Dutko, "Conformational Change in the floor of the Human Rhinovirus Canyon Blocks Adsorption to HeLa Cell Receptors", J. Virol. 63(5): 2002–2007 (May 1989).

Plow, E. F., M.D. Pierschbacher, E. Ruoslahti, G.A. Marguerie, and M.H. Ginsberg, "The effect of Arg–Gly–Asp––containing peptides on fibrinogen and von Willebrand factor binding to platelets", Proc. Natl. Acad. Sci. USA 82: 8057–8061 (1985).

Ray, C.G., "Chapter 32: Respiratory Viruses", in *Medical Microbiology, an Introduction to Infectious Diseases*, 2nd Ed., J. C. Sherris, ed. (Elsevier, New York, 1990), pp. 499–516.

Roesing, T. G., P. A. Toselli, R.L. Crowell, "Elution and Uncoating of Coxsackievirus B3 by Isolated HeLa Cell Plasma Membranes", J. Virol. 15(3): 654–667 (Mar. 1975).

Rossmann, M. G., "The Canyon Hypothesis. Hiding the Host Cell Receptor Attachment Site on a Viral Surface from Immune Surveillance", J. Biol. Chem. 264(25): 14587–14590 (Sep. 1989).

Saiki, R.K., D.H. Gelfand, S. Stoffel, S.J. Scharf, R. Higuchi, G.T. Horn, K.B. Mullis, and H.A. Erlich, "Primer–Directed Enzymatic Amplification of DNA with a Thermostable DNA Polymerase", Science 239: 487–491 (Jan. 1988).

Sayre, P.H., R.E. Hussey, H.–C. Chang, T.L. Ciardelli, and E.L. Reinherz, "Structural and Binding Analysis of a Two Domain Extracellular CD2 Molecule", J. Exp. Med. 169: 995–1009 (Mar. 1989).

Siu, G., S.M. Hedrick, and A.A. Brian, "Isolation of the Murine Intercellular Adhesion Molecule 1 (ICAM–1) Gene", J. Immun. 143(11): 3813–3820 (Dec. 1989).

Skern, T., W. Sommergruber, D. Blass, P. Gruendler, F. Fraundorfer, C. Pieler, I. Fogy, and E. Kuechler, "Human rhinovirus 2: complete nucleotide sequence and proteolytic processing signals in the capsid protein region", Nucleic Acids Research 13(6): 2111–2126 (1985).

Smilek, D. E., D.C. Wraith, S. Hodgkinson, S. Swivedy, L. Steinman, and H.O. McDevitt, "A single amino acid change in a myelin basic protein peptide confers the capacity to prevent rather than induce experimental autoimmune encephalomyelitis", Proc. Natl. Acad. Sci. USA 88: 9633–9637 (Nov. 1991).

Staunton, D.E., M.L. Dustin, and T.A. Springer, "Functional cloning of ICAM–2, a cell adhesion ligand for LFA–1 homologous to ICAM–1", Nature 339: 61–64 (May 1989).

Staunton, D.E., C.F. Ockenhouse, and T.A. Springer, "Soluble Intercellular Adhesion Molecule 1–Immunoglobulin G1 Immunoadhesin Mediates Phagocytosis of Malaria–infected Erythrocytes", J. Exp. Med. 176: 1471–1476 (Nov. 1992).

Uncapher, C. R., C.M. DeWitt, and R.J. Colonno, "The Major and Minor Group Receptor Families Contain All but One Human Rhinovirus Serotype", Virology 180: 814–817 (1991).

Wickner W. T., and H.F. Lodish, "Multiple Mechanisms of Protein Insertion Into and Across Membranes", Science 230: 400–407 (Oct. 1985).

Weis, W., J.H. Brown, S. Cusack, J.C. Paulson, J.J. Skehel, and D.C. Wiley, "Structure of the influenza virus haemagglutinin complexed with its receptor, sialic acid", Nature 333: 426–431 (Jun. 1988).

R&D Systems (Minneapolis, MN), 1994 Catalog, Item # BBE 1B, "Human Soluble ICAM–1".

"Chapter 9, Introduction of DNA into Mammalian Cells", Current Protocols in Molecular Biology 1997:9.0.1–9.9.16 (1977).

British Biotechnology, Ltd. (Oxford, England), 1993 Product Catalog, Item # BBE 1, "Soluble ICAM–1 ELISA".

Abraham, G. and R.J. Colonno, "Characterization of human rhinoviruses displaced by an anti–receptor monoclonal antibody", J. Virol.62(7):2300–2306 (Jul. 1988).

Ashkenzai, A., L.G. Presta, S.A. Marsters, T.R. Camerato, K.A. Rosen, B.M. Fendly, and D.J. Capon, "Mapping the CD4 binding site for human immunodeficiency virus by alanine scanning mutagenesis", Proc. Natl. Acad. Sci. USA 87:7150–7154 (Sep. 1990).

Brodsky, M.H., M. Warton, R.M. Myers, and D.R. Littman, "Analysis of the site in CD4 that binds to the HIV envelope glycoprotein", J. Immunol. 144(8):3078–3086 (Apr. 1990).

Callahan, P.L., S. Mizutani, and R.J. Colonno, "Molecular cloning and complete sequence determination of RNA genome of human rhinovirus type 14", Proc. Natl. Acad. Sci. USA 82(3):732–6 (Feb. 1985).

Colonno, R.J., "Virus receptors: the Achilles' heel of human rhinoviruses", in Innovations in Antiviral Development and the Detection of Virus Infection, T. Block et al., eds., (Plenum Press, NY, 1992), pp. 61–70.

Colonno, R.J., P.L. Callahan, D.M. Leippe, R.R. Rueckert, and J.E. Tomassini, "Inhibition of rhinovirus attachment by neutralizing monoclonal antibodies and their Fab fragments," J. Virol. 63(1):36–42 (Jan. 1989).

Colonno, R.J., "Cell surface receptors for picornaviruses", Bioassays 5(6):270–4 (1986).

Colonno, R.J., "Molecular interactions between human rhinoviruses and their cellular receptors", Seminars in Virol. 3(2):101–107 (1992).

Colonno, R.J., R.L. LaFemina, C.M. DeWitt, and J.E. Tomassini, "The major–group rhinoviruses utilize the intercellular adhesion molecule 1 ligand as a cellular receptor during infection", in *New Aspects of Positive–Strand RNA Viruses,* Second International Symposium, Vienna, Austria, Meeting Date 1989, Brinton et al., eds. (Am. Soc. Microbiol., Washington, DC, 1990), pp. 257–261.

Colonno, R.J., G. Abraham, and J.E. Tomassini, "Molecular and biochemical aspects of human rhinovirus attachment to cellular receptors", in *Molecular Aspects of Picornavirus Infection and Detection,* [Presentations ICN–UCI Int. Conf. Virol.], Meeting Date 1988, Semler et al., eds. (Am. Soc. Microbiol., Washington, DC, 1989), pp. 169–178.

Colonno, R.J., J.E. Tomassini, P.L. Callahan, and W.J. Long, "Characterization of the cellular receptor specific for attachment of most human rhinovirus serotypes", in *Virus Attachment Entry Cells,* Proc. ASM Conf., Meeting Date 1985, Crowell et al., eds. (Am. Soc. Microbiol. Washington, DC, 1986), pp. 109–115.

Colonno, R.J., "Molecular interactions between human rhinoviruses and the adhesion receptor ICAM–1", in *Microb. Adhes. Invasion,* [Proc. Symp.], meeting date 1990, Hook et al., eds. (Springer, NY, 1992), pp. 33–41.

Colonno, R.J., J.H. Condra, and S. Mizutani, "Interaction of cellular receptors with the canyon structure of human rhinoviruses", in *UCLA Symposia on Molecular and Cellular Biology New Series, vol. 90, Cell Biology of Virus Entry, Replication, and Pathogenesis, Taos, NM, Feb. 28–Mar. 5, 1988,* Compans et al., eds. (Alan R. Liss, Inc., NY, 1988) pp. 75–84.

Colonno, R.J., R. B. Register, D. W. Lineberger, and C.R. Uncapher, "Identification of ICAM–1 residues critical for attachment of human rhinoviruses", Meeting on Molecular Biology of Human Pathogenic Viruses held at the 20th Annual Meeting of the Keystone Symposia on Molecular and Cellular Biology, Lake Tahoe, CA, Mar. 8–15, 1991, J. Cell Biochem. Suppl. 15(Part E):82, #M310 (1991).

Colonno, R.J., J.H. Condra, S. Mizutani, G. Abraham, P.L. Callahan, J.E. Tomassini, and M.A. Murcko, "Evidence for direct involvement of the rhinovirus canyon with cellular receptors", in *Symposium on Cell Biology of Virus Entry, Replication and Pathogenesis, Positive Strand RNA Viruses,* 17th Annual UCLA meeting on Molecular and Cellular Biology, Taos, NM, Feb. 28–Mar. 5, 1988, J. Cell. Biochem. Suppl., 0(12 Part C):4, #J005 (1988).

Colonno, R.J., J.E. Tomassini, and P.L. Callahan, "Isolation and characterization of a monoclonal antibody which blocks attachment of human rhinoviruses", in *UCLA Symposia on Molecular and Cellular Biology,* New Series, vol. 54, Positive Strand RNA Viruses, Keystone, CO Apr. 20–26, 1986, Brinton et al., eds. (Alan R. Liss, Inc., NY, 1987), pp. 93–102.

Colonno, R.J., J.E. Tomassini, and P.L. Callahn, "Human rhinovirus attachment requires a specific cellular receptor protein", in *Symposium on Positive Strand RNA Viruses,* 15th Annual Meeting of the UCLA Symposia on Molecular and Cellular Biology, Apr. 20–26, 1986, J. Cell. Biochem Suppl., 0(10 Part D):266, #Q4 (1986).

Condra, J.H., V.V. Sardan, J.E. Tomassini, A.J. Schlabach, M.–E. Davies, D.W. Lineberger, D.J. Graham, and R.J. Colonno,, "Bacterial expression of antibody fragments that block human rhinovirus infection of cultured cells", J. Biol. Chem. 265(4):2292–2295 (Feb. 1990).

Cordingley, M.G., P.L. Callahan, V.V. Sardana, V.M. Garsky, and R.J. Colonno, "Substrate requirements of human rhinovirus 3C protease for peptide cleavage in vitro", J. Biol. Chem. 265(16):9062–5 (1990).

Cordingley, M.G., R.B. Register, P.I. Callahan, V.M. Garsky, and R.J. Colonno, "Cleavage of small peptides in vitro by human rhinovirus 14 3C protease expressed in *Escherichia coli*", J. Virol. 63(12):5037–45 (Dec. 1989).

Dewalt, P.G., M.A. Lawson, R.J. Colonno, and B.L. Semler, "Chimeric picornavirus polyproteins demonstrate a common 3C proteinase substrate specificity", J. Virol. 63(8):3444–3452 (1989).

Dick, E.C., and C.R. Dick, "Natural and Experimental Infections of Nonhuman Primates with Respiratory Viruses", Laboratory Animal Science 24(1): 177–181 (1974).

Emini, E.A., W.A. Schleif, R.J. Colonno, and E. Wimmer, "Antigenic conservation and divergence between the viral––specific proteins of poliovirus type 1 and various picornaviruses", Virol. 140(1):13–20 (1985).

Hazuda, D., V. Sardana, P. Callahan, M. Cordingley, and R. Colonno, "Chemical approaches to mapping the active site thiol of human rhinovirus 3C protease", Joint Meeting of the American Society for Biochemistry and Molecular Biology and the American Association of Immunologists, New Orleans, LA, Jun. 4–7, 1990, Fed. Am. Soc. Exp. Biol. J. 4(7):#1605 (1990).

Johnston, S.C., M.L. Dustin, M.L. Hibbs, and T.A. Springer, "On the species specificity of the interaction of LFA–1 with intercellular adhesion molecules", J. Immunol. 145(4):1181–1187 (Aug. 1990).

Lamarre, D., D.J. Capon, D.R. Karp, T.Gregory, E.O. Long, and R.–P. Sekaly, "Class II MHC molecules and the HIV envelope glycoprotein interact with functionally distinct regions of the molecule", EMBO J. 8(11):3271–3277 (1989).

Lineberger, D.W., C.R. Uncapher, D.J. Graham, and R.J. Colonno, "Domains 1 and 2 of ICAM–1 are sufficient to bind human rhinoviruses", Virus Research 24(2): 173–86 (1992).

Maddon, P.J., A.G. Dalgleish, J.S. McDougal, P.R. Clapham, R.A. Weiss, and R. Axel, "The T4 Gene Encodes the AIDS Virus Receptor and is Expressed in the Immune System and the Brain", Cell 47:333–348(Nov. 1986).

Mendelsohn, C.L., E. Wimmer, and V.R. Racaniello, "Cellular receptor for poliovirus: molecular cloning, nucleotide sequence, and expression of a new member of the immunoglobulin superfamily", Cell 56:855–865 (Mar. 1989).

Mizutani, S., and R.J. Colonno, In vitro synthesis of an infectious RNA from cDNA clones of human rhinovirus type 14:, J. Virol. 56(2):628–32 (Nov. 1985).

Register, R.B., C.R. Uncapher, A.M. Naylor, D.W. Lineberger, and R.J. Colonno, "Human–murine chimeras of ICAM–1 identify amino acid residues critical for rhinovirus and antibody binding", J. Virol. 65(12):6589–6596 (Dec. 1991).

Rueckert, R. B. Sherry, A. Mosser, R. Colonno, and M. Rossman, "Location of four neutralization antigens on the three–dimensional surface of a common–cold picornavirus, human rhinovirus 14", in *Virus Attachment Entry Cells,* Proc. ASM Conf., Meeting date 1985, Crowell et al., eds. (Am. Soc. Microbiol., Washington, DC, 1986), pp. 21–27.

Sherry, B., A.G. Mosser, R.J. Colonno, and R.R. Rueckert, "Use of monoclonal antibodies to identify four neutralizing immunogens on a common cold picornavirus, human rhinovirus 14", J. Virol. 57(1):246–57 (Jan. 1986).

Tomassini, J.E., T.R. Maxson, and R.J. Colonno, "Biochemical characterization of a glycoprotein required for rhinovirus attachment", J. Biol. Chem. 264(3):1656–1662 (Jan. 1989).

Tomassini, J.E., and R.J. Colonno, "Isolation and characterization of a cellular receptor involved in attachment of human rhinoviruses to cells", in *Symposium on Positive Strand RNA Viruses,* $15^{th}$ Annual Meeting of the UCLA Symposia on Molecular and Cellular Biology, Apr. 20–26, 1986, J. Cell. Biochem. Suppl., 0(10 Part D):300,#Q92 (1986).

SOLUBLE TRUNCATED FORMS OF ICAM-1

This application is a divisional of copending application U.S. Ser. No. 08/316,386 filed Sep. 30, 1994, which is a continuation of U.S. Ser. No. 08/103,610 filed Aug. 6, 1993, now abandoned, which is a continuation of U.S. Ser. No. 07/704,996 filed May 24, 1991, now abandoned, which is a continuation-in-part of U.S. Ser. No. 07/631,313 filed Dec. 20, 1990, now abandoned, which is a continuation-in-part of U.S. Ser. No. 07/556,238 filed Jul. 20, 1990, now abandoned, and a continuation-in-part of U.S. Ser. No. 07/390,662, filed Aug. 10, 1989, now abandoned, which is a continuation-in-part of U.S. Ser. No. 07/239,571 filed Sep. 1, 1988, now abandoned, and a continuation-in-part of U.S. Ser. No. 07/262,428 filed Oct. 25, 1988, now abandoned, which is a continuation-in-part of U.S. Ser. No. 07/239,571 filed Sep. 1, 1988, now abandoned.

BACKGROUND OF THE INVENTION

The present invention relates to novel truncated forms of intercellular adhesion molecule (ICAM), designated "tICAMs", which effectively bind to human rhinovirus (HRV) and to lymphocyte-function associated antigen-1 (LFA-1). The present invention also pertains to DNA sequences coding for various tICAMs and to methods for preventing or amelio-rating infection and inflammation using said tICAMs.

Human rhinoviruses, the major causative agent of the common cold, belong to the picornavirus family. There are more than 100 distinct serotypes of human rhinovirus. The three-dimensional structure of several rhinovirus sero-types have now been determined to atomic resolution by Rossmann, M. G., E. Arnold, J. W. Erickson, E. W. Frankenberger, P. J. Griffith, H. Hecht, J. E. Johnson, G. Kamer, M. Luo, A. G. Mosser, R. R. Rueckert, B. Sherry, and G. Vriend, "Structure of a common cold virus and functional relationship to other picornaviruses", Nature (1985) 317:145–153; and Kim, S., T. J. Smith, M. M. Chapman, M. G. Rossmann, D. C. Pevearj, F. J. Dutko, P. J. Felock, G. D. Diana, and M. A. McKinlay, "Crystal structure of human rhinovirus serotype 1A (HRV1A)", J. Mol. Biol. (1990) 210:91–111. The virion is composed of a protein capsid of 60 protomeric units, consisting of the four protein subunits VP1–4, surrounding an RNA genome. Each of the 60 protomeric units possesses a recessed 30-angstrom-wide depression or "canyon" which encircles the five-fold axis of symmetry of each icosahedral face of the virus and which is believed to contain the site that binds to the receptor on the target cell surface [reviewed in Rossmann,, M. G., J. Biol. Chem. (1989) 264:14587–14590].

In order to infect host cells, viruses must bind to and then enter cells to initiate an infection. Since 1959, evidence has accumulated in the literature indicating that the presence of specific binding sites (receptors) on host cells could be a major determinant of tissue tropism of certain viruses. [Holland, J. J., and L. C. McLaren, "The mammalian cell-virus relationship. II. Absorption, reception, and eclipse of poliovirus by HeLa cells," J. Exp. Med. 109:487–504 (1959); Holland, J. J., "Receptor affinities as major determinants of enterovirus tissue tropisms in humans," Virology 15:312–326 (1961)]. Specific binding to host cells has been demonstrated among picornaviruses such as poliovirus, Coxsackie virus, and rhinoviruses. By competition experiments, it has been demonstrated that some of these receptors are distinct from one another in that the saturation of the receptor of one virus had no effect on the binding of a second virus. [Lonberg-Holm, K., R. L. Crowell, and L. Philipson. "Unrelated animal viruses share receptors," Nature 259:679–681 (1976)].

Rhinoviruses can be classified according to the host cell receptor to which they bind. Tomassini, J. E. and R. J. Colonno, "Isolation of a receptor protein involved in attachment of human rhinoviruses," J. Virol. 58:290 (1986) reported the isolation of a receptor protein involved in the cell attachment of HRV. Approximately 90% of the more than 115 serotypes of rhinoviruses, as well as several types of Coxsackie A virus, bind to a single common receptor termed the "major" human rhinovirus receptor (HRR) [Abraham, G., and R. J. Colonno, "Many rhinovirus serotypes share the same cellular receptor," J. Virol. 51:340–345 (1984)]; the remaining 10% bind to one or more other cell receptors.

The major human rhinovirus receptor has been transfected, identified, purified, and reconstituted as described in co-pending U.S. patent applications Ser. No. 07/262,428 and 07/262,570, both filed Oct. 25, 1988. Greve, J. M., G. Davis, A. M. Meyer, C. P. Forte, S. C. Yost, C. W. Marlor, M. E. Kamarck, and A. McClelland, "The major human rhinovirus receptor is ICAM-1," Cell 56:839–847 (1989), identified the major HRR as a glycoprotein with an apparent molecular mass of 95 kD and having an amino acid sequence essentially identical to that deduced from the nucleotide sequence of a previously described cell surface protein named intercellular adhesion molecule (ICAM-1). ICAM-1 had first been identified based on its role in adhesion of leukocytes to endothelial cells [Rothlein, R., et al., J. Immunol. 137:1270–1274 (1986); see also Simmons, D., M. W. Makgoba, and B. Seed, "ICAM-1, an adhesion ligand of LFA-1, is homologous to the neural cell adhesion molecule NCAM", Nature (1988) 331:624–627; Staunton, D. E., S. D. Marlin, C. Stratowa, M. L. Dustin, and T. A. Springer, "Primary structure of ICAM-1 demonstrates interaction between members of the immunoglobulin and integrin supergene families," Cell (1988) 52:925–933.] Induction of ICAM-1 expression by cytokines during the inflammatory response may regulate leukocyte localization to inflammatory sites. Subsequently, Staunton, D. E., et al., Cell 56:849 (1989) confirmed that ICAM-1 is the major cell surface receptor for HRV. See also Staunton, D. E., M. L. Dustin, H. P. Erickson, and T. A. Springer, "The arrangement of the immunoglobulin-like domains of ICAM-1 and the binding sites for LFA-1 and rhinovirus," Cell (1990) 61:243–254.

European Patent Application 0 289 949 describes membrane-associated ICAM-1, which mediates attachment of many cell types, including endothelial cells, to leukocytes expressing lymphocyte function associated molecule-1 (LFA-1; CD18/CD11a, a member of the beta-2 integrin family). Said patent application provides a discussion of the prior research in the field of intercellular adhesion molecules.

Heterotypic binding of the leukocyte integrin LFA-1 to ICAM-1 mediates cellular adhesion of diverse cell types and is important in a broad range of immune interactions [Marlin, et al., Cell (1987) 51:813–819]. ICAM-1 also binds to MAC-1 (CD18/CD11b), another beta-2 integrin, but not to p150/95 (CD18/CD11c) [Staunton et al., Cell (1988) 52:925–933]. MAC-1 and p150/95 differ from LFA-1 by their alpha subunit. Although minimal peptide recognition sites have been identified for many other integrins, the recognition site for LFA-1 on ICAM-1 remains obscure. Staunton, et al., Cell (1990) 61:243–254 have reported that a transmembrane form of the first two domains of ICAM-1 retains some LFA-1-binding activity and that a number of mutations in the first two domains of the full-length molecule cause reductions in LFA-1-binding activity.

The primary structure of ICAM-1 is homologous to two other cellular adhesion molecules: neural cell adhesion molecule (NCAM) and myelin-associated glycoprotein (MAG). This suggests that ICAM-1 is a member of the immunoglobulin supergene family [Simmons, et al., Nature (1988) 331:624–627; Staunton et al., Cell (1988) 52:925–933]. The CDNA sequences for ICAM-1 are described in the above-referenced papers by Simmons et al. and Staunton et al., from which the amino acid sequence of ICAM-1 has been deduced.

ICAM-1 is an integral membrane protein 505 amino acids long [SEQ ID NO: 1; encoded by nucleotides 139–1653 of SEQ ID NO: 2] and has: i) five immunoglobulin-like extracellular domains at the amino-terminal (extracellular) end (designated domain I [amino acid residues 1–88], domain II [89–185], domain III [186–283], domain IV [284–385], and domain V [386–453]); [Staunton, et al., Cell (1988) 52:925–933]; ii) a hydrophobic transmembrane domain (454–477); and iii) a short cytoplasmic domain at the carboxy-terminal end (478–505). The sequences of the first three domains can be aligned with immunoglobulins in a manner consistent with structural homology to the IgG constant region fold [reviewed by Williams, A. F. and A. N. Barclay, "The immunoglobulin superfamily—domains for cell surface recognition", Ann. Rev. Immunol. (1988) 6:381–405]. The IgG fold consists of two beta sheets comprised of anti-parallel beta strands A. B, E and D on one face and C, F, and G on the other (see FIG. 1). The sheets interact to form a hydrophobic interior and individual strands are linked by loops of variable length. The N-terminal loops of antibody variable regions form the antigen combining site. As shown in Example 7. below, circular dichroism spectra of the extracellular portion of ICAM-1 indicate that the molecule contains substantial amounts of beta structure, supporting the proposed IgG-fold structure for ICAM-1 domains.

As mentioned above, the three-dimensional structure of HRV-14 which binds to ICAM-1 and of ERV-1A which binds to the as yet unidentified minor receptor have been determined [Rossman, M. G., E. Arnold, T. W. Erickson, E. W. Frankenberger, P. J. Griffith, H. Hecht, J. E. Johnson, G. Kamer, M. Luc, A. G. Mosser, R. R. Rueckert, B. Sherry, and G. Vriend, "Structure of a common cold virus and functional relationship to other picornaviruses", Nature (1985) 317:145–153; Kim, S., T. J. Smith, M. M. Chapman, M. G. Rossmann, D. C. Pevear, F. J. Dutko, P. J. Felock, G. D. Diana, and M. A. McKinlay, "Crystal structure of human rhinovirus serotype 1A (HRV1A)", J. Mol. Biol. (1989) 210:91–111] and a "canyon" model of the viral binding site has been proposed. Residues in the lower part of the canyon are inaccessible to antibody molecules and thus the conserved receptor binding determinants could escape immune surveillance. Support for the canyon hypothesis comes from site-directed mutagenesis of canyon residues which alter the receptor binding properties of HRV-14 [Colonno, R. J., J. H. Condra, S. Mizutani, P. L. Callahan, M. E. Davies, and M. A. Murcko, "Evidence for the direct involvement of the rhinovirus canyon in receptor binding", Proc. Natl. Acad. Sci. USA (1988) 85:5449–5453], and from studies with capsid-binding drugs which induce a conformational change in the floor of the canyon and prevent receptor binding [Pevear, D. C., M. J. Fancher, P. J. Felock, M. G. Rossmann, M. S. Miller, G. Diana, A. M. Treasurywala, M. McKinlay, and F. J. Dutkor "Conformational change in the floor of the human rhinovirus canyon blocks adsorption to HeLa cell receptors," J. Virol. (1989) 63:2002–2007]. The dimensions of the rhinovirus canyon are sufficiently large to accommodate a single unpaired IgG domain, and it has recently been shown by electron microscopy that ICAM-1 and the related adhesion molecule NCAM have long elongated structures consistent with an end-to-end arrangement of-unpaired IgG domains [Staunton et al., Cell (1990) 61:243–254; Becker, J. W., H. P. Erickson, S. Hoffman, B. A. Cunningham, and G. M. Edelman, "Topology of cell adhesion molecules", Proc. Natl. Acad. Sci. USA (1989) 86:1088–1092]. The N-terminal domain of ICAM-1 is therefore likely to project furthest from the cell surface and be most accessible to virus. Furthermore, ICAM-1 is heavily glycosylated with the exception of the first domain. While the precise configuration of the virus-binding site on ICAM-1 remains to be determined, Staunton et al., Cell (1990) 61:243–254 have shown by site-directed mutagenesis and construction of a human/mouse chimera that the rhinovirus binding site is contained within the first two N-terminal domains of ICAM-1. A three-dimensional model of the first domain of ICAM-1 based on alignment with known immunoglobulin structures was docked with the rhinovirus canyon and used to predict possible contact residues [Giranda, V. L., M. S. Chapman, and M. G. Rossmann, "modeling of the human intercellular adhesion molecule-1, the human rhinovirus major group receptor", Proteins (1990) 7:227–233].

Several approaches to decreasing infectivity of viruses in general, and of HRV in particular, have been pursued including: i) developing antibody to the cell surface receptor for use in blocking viral binding to the cell; ii) using interferon to promote an anti-viral state in host cells; iii) developing various agents to inhibit viral replication; iv) developing antibodies to viral capsid proteins/peptides; and v) blocking viral infection with isolated cell surface receptor protein that specifically blocks the binding domain of the virus.

In 1985, the isolation of a monoclonal antibody that appeared to be directed against the major rhinovirus receptor was described. [Colonno, R. J., P. L. Callahan, and W. J. Long, "Isolation of a monoclonal antibody that blocks attachment of the major group of human rhinoviruses," J. Virol. 57:7–12 (1986)]. This monoclonal inhibited infection of cells with the appropriate serotypes of rhinovirus and it inhibited binding of radiolabeled rhinovirus to cells. Colonno et al. subsequently reported that the monoclonal antibody bound to a protein with an apparent molecular weight of 90 kD [Tomassini, et al., J. Virol. (1986) 58:290–295]. This monoclonal antibody has been utilized in clinical trials with primates and humans and is understood to provide some protection against rhinovirus infection.

There are several other reports of attempts at therapeutic intervention in rhinovirus infections. Intranasal application of interferon in humans has been attempted. [Douglas, R. M. et al., "Prophylactic efficacy of intranasal alpha2-interferon against rhinovirus infections in the family setting," N. Eng. J. Med. 314:65–75 (1986)]. In this case, significant reduction in the severity of the infection was found, although nosebleeds were observed as a side-effect. Also, several analogs of disoxaril ("WIN" compounds) that reduce the infectivity of a number of picornaviruses (with widely varying effectiveness, depending on the serotype) have been tested in tissue culture and in some animal models [Fox, M. P., M. J. Otto, and M. A. McKinlay, Antimicrob. Ag. and Chemotherapy (1986) 30:110–116]. These compounds appear to inhibit replication at a step subsequent to receptor binding, probably at some step of virus uncoating. The atomic coordinates of the binding sites of these compounds within the viral capsid of the serotype HRV14 have been determined by x-ray crystallography, and are located in a hydrophobic pocket present in each protomeric unit of the capsid [Smith, T. J., et al., "The site of attachment in human rhinovirus 14 for antiviral agents that inhibit uncoating," Science (1986) 233:1286–1293]. The specific function of the binding pocket, if any, is unknown, but drug-resistant mutants with a single amino acid interchange in this region arise at high frequency and are viable [Badger, J., et al., "Structural analysis of a series of antiviral agents complexed with human rhinovirus 14," Pas 85:3304–3308 (1988); see also Dearden et al., Arch. Virol. (1989) 109:71]. This result calls into question the efficacy of such compounds as drugs.

The production of anti-peptide antibodies in rabbits has been reported using peptides derived from amino acid sequences of the viral capsid proteins that line the "receptor canyon" of HRV14 [McCray, J., and G. Werner, "Different rhinovirus serotypes neutralized by antipeptide antibodies," Nature (1987) 329:736–738]. While the titers of these sera are quite low, cross-serotype protection of cells in tissue culture from rhinovirus infection was demonstrated, raising the possibility of a vaccine.

It is an object of the present invention to provide an HRV receptor protein having the property of blocking HRV infection. Given the high affinity the virus has for its receptor, a therapeutic agent effective against HRV infection is the receptor itself, or more specifically, the virus-binding domain of the receptor. A protein, protein fragment, or peptide that comprises the virus-binding domain can block the ability of virus to bind to host cells by occupying (blocking) the receptor-binding cleft on the virus. Furthermore, since such a molecule makes some or all of the molecular contacts with the virus capsid that the receptor does, any viral mutations that would evade binding of the therapeutic molecule would also adversely affect binding of the natural receptor, and thus would be are deleterious or lethal for the virus; therefore, the likelihood of drug-resistant mutants is very low.

Using this approach, Greve, et al., Cell (1989) 56:879, [U.S. Ser. No. 07/239,571, filed Sep. 1, 1988] showed that purified transmembrane ICAM-1 (tmICAM-1) could bind to rhinovirus HRV3 in vitro. Other results with HRV2, HRV3, and HRV14 demonstrated a positive correlation between the ability to bind to rhinovirus and the ability to neutralize rhinovirus. Results using HRV14 and HRV2 demonstrated a positive correlation between the receptor class of the virus and the ability to bind to tmICAM-1 in vitro. That is, ICAM-1, being the major receptor, binds to HRV3, HRV14, and other major receptor serotypes and neutralizes them, while it does not bind or neutralize HRV2, a minor receptor serotype. Further studies, using purified tmICAM-1, demonstrated that it effectively inhibits rhinovirus infectivity in a plaque-reduction assay when the rhinovirus is pretreated with tmICAM-1 (50% reduction of titer at 10 nM receptor and one log reduction of titer at 100 nM receptor protein). These data were consistent with the affinity of rhinovirus for ICAM-1 of HeLa cells, which has an apparent dissociation constant of 10 nM, and indicates a direct relationship between the ability of the receptor to bind to the virus and to neutralize the virus.

The ICAM of the prior art is an insoluble molecule which is solubilized from cell membranes by lysing the cells in a non-ionic detergent. Because large-scale production of tmICAM-1 is not presently economically feasible, and because maintenance of tmICAM-1 in an active form requires the use of detergents, alternate soluble forms of receptor protein suitable for use as a rhinovirus inhibitor are desirable. See generally copending applications U.S. Ser. No. 07/130,378; U.S. Ser. No. 07/239,571; U.S. Ser. No. 07/262,428; U.S. Ser. No. 262,570; U.S. Ser. No. 07/301,192; U.S. Ser. No. 07/390,662; U.S. Ser. No. 07/449,356; U.S. Ser. No. 07/678,909; and U.S. Ser. No. 07/631,313, all incorporated herein by reference.

U.S. Ser. No. 07/130,378 (filed Dec. 8, 1987) and its CIP application U.S. Ser. No. 07/262,570 are directed to transfected non-human cell lines which express the major human rhinovirus receptor (HRR), and to the identification of HRR as intercellular adhesion molecule (ICAM).

U.S. Ser. No. 07/301,192 (filed Jan. 24, 1989) and its CIP applications U.S. Ser. No. 07/445,951 (abandoned) and U.S. Ser. No. 07/449,356 are directed to a naturally-occurring soluble ICAM (sICAM) related to but distinct from tmICAM in that said sICAM lacks the amino acids spanning the hydrophobic transmembrane region and the carboxy-terminal cytoplasmic region; in addition this sICAM has a novel sequence of 11 amino acids at its C-terminus.

Parent application U.S. Ser. No. 07/239,571 (filed Sep. 1, 1988) and its CIP applications U.S. Ser. No. 07/262,428 and U.S. Ser. No. 07/390,662 (abandoned in favor of continuation U.S. Ser. No. 07/678,909), and U.S. Ser. No. 07/631,313 are directed to the use of detergent-complexed tmICAM as an inhibitor of HRV infectivity, using the non-ionic detergent complex to maintain the transmembrane protein in solution. These cases are also directed to truncated forms of ICAM (tICAMs) comprising one or more of the extracellular domains I, II, III, IV, and V of tmICAM, which truncated forms do not require the presence of non-ionic detergent for solubilization. See FIG. 2.

Parent application U.S. Ser. No. 07/556,238 (filed Jul. 20, 1990) is directed to multimeric configurations of tmICAM-1 and tICAM-1 having improved ability to prevent HRV Infection. When tmICAM-1 or tICAMs are presented in a dimer configuration, the virus-binding activity of the dimerized ICAM becomes comparable to that of native tmICAM-1. This binding of multimeric ICAMs to HRV has the same properties as the binding of HRV to ICAM-1 on HeLa cells: it is inhibited by anti-ICAM-1 monoclonal antibodies, it is specific for HRV of the major receptor group, and it has the same temperature-dependence pattern as the binding of HRV to cells (i.e., binds well at 37° C. and undetectably at 4° C.).

The present application contains further data demonstrating the properties and efficacy of various forms of tICAM.

SUMMARY OF THE INVENTION

The present invention provides truncated forms of ICAM-1 designated tICAMs which are soluble without the addition of a detergent.

The present invention also provides purified and isolated tICAMs, or functional derivatives thereof, substantially free of natural contaminants.

The present invention further provides a purified and isolated DNA sequence encoding tICAMs as well as host cells encoding said sequences.

The present invention provides a method of recovering tICAMs in substantially pure form comprising the steps of cloning a genome coding for the desired tICAM form in a suitable expression vector in a suitable host.

Also provided by the invention are novel pharmaceutical compositions comprising a pharmaceutically acceptable solvent, diluent, adjuvant or carrier, and as the active ingredient, an effective amount of a polypeptide characterized by having HRV binding activity and reduction of virus infectivity.

The present invention includes monoclonal antibodies against ICAM-1 and tICAMs, and hybridoma cell lines capable of producing such monoclonal antibodies.

This invention further includes the therapeutic use of antibodies specifically directed to tICAMs to decrease cell adhesion mediated by ICAM-1 and LFA-1.

The invention further includes a method of inhibiting LFA-1 and ICAM-1 interaction comprising the step of contacting LFA-1-containing cells with a tICAM or a functional derivative thereof.

A further aspect of the invention is use of fragments, functional domains or analogs of LFA-1 to disrupt interactions between HRR and HRV and thereby treat HRV infections.

This invention further includes a method for substantially reducing Infection by HRV of the major receptor group, comprising the step of contacting the virus with a tICAM or a functional derivative thereof.

This invention further includes a method for substantially reducing infection by other pathogens of the major HRR group, e.g., Coxsackie virus and *Plasmodium falciparum*, comprising the step of contacting the pathogen with one or more tICAMs or functional derivatives thereof.

The invention further comprises a method for substantially reducing infection by picornaviruses, comprising contacting viruses of the picornavirus family with one or more adhesion proteins selected from the group consisting of tICAMs and myelin-associated glycoprotein, and mixtures thereof.

The invention further comprises a method for enhancing the binding of a tICAM to a ligand, said improvement comprising the steps of presenting said compound in a form and configuration to said ligand wherein binding of said compound to said ligand is enhanced.

The invention further comprises a method of treating inflammation, said method comprising inhibiting LFA-1 and ICAM interaction by contacting ICAM-containing cells with inactivated human rhinovirus.

The invention further comprises a method of inhibiting binding of monoclonal antibody c78.4A to an ICAM, said method comprising altering one or more of the following moieties in said ICAM amino acid sequence: Lys-40, Leu-43, Lys-40/Glu-41/Leu-62/Leu-43 [SEQ ID NO: 3].

The invention further comprises a method of inhibiting binding of monoclonal antibody c78.5A to an ICAM, said method comprising altering one or more of the following moieties in said ICAM amino acid sequence: Asp-71, Gly-72, Pro-70/Asp-71/Gly-72, Asp-26/Gln-27/Pro-28/Lys-29 [SEQ ID NO: 4].

The invention further comprises a method of inhibiting binding of human rhinoviruses to an ICAM, said method comprising altering one or more of the following moieties in said ICAM amino acid sequence: Met-64/Cys-65/Tyr-66, Lys-40, Leu-43, Asp-71, Pro-70/Asp-72/Gly-73. Asp-26/Gln-27/Pro-28/Lys-29 [SEQ ID NO: 4], Asp-71/Gly-72, Leu-30/Leu-31/Gly-32/Ile-33 [SEQ ID NO: 5], Thr-75/Ala-76/Lys-77.

The invention further comprises a method of improving binding of human rhinovirus to an ICAM, said method comprising altering one or more of the following moieties in said ICAM amino acid sequence: Pro-36, Leu-37, Pro-38.

Other aspects and advantages of the present invention will be apparent upon consideration of the following detailed description which includes numerous illustrative examples of the practice of the invention.

BRIEF DESCRIPTION OF THE DRAWINGS

FIG. 1 is a schematic diagram illustrating the three-dimensional structure of ICAM-1 [Williams, A. F. and A. N. Barclay, "The immunoglobulin superfamily—domains for cell surface recognition", Ann. Rev. Immunol. (1988) 6:381–405.

FIG. 2 shows secretion of soluble ICAM-1 proteins. (A) Diagram of progressively truncated forms of ICAM-1 used in transfection experiments. Crosshatched region indicates signal sequence, filled region indicates the transmembrane region, Roman numerals indicate domains; (B) Fluorograph of [$^{35}$S]cysteine-labelled products secreted by COS cells analyzed by SDS-PAGE; loading of lanes containing tICAM (283) and tICAM(88) is 10-fold higher than other lanes; (C) Silver-stained gel of purified tICAM(453) and tICAM(185) produced by Chinese hamster cell (CHO) transfectants.

FIG. 3 shows inhibition of rhinovirus binding by anti-ICAM-1 monoclonal antibodies. HeLa cell monolayers in 24-well microtiter plates were pre-incubated with the indicated concentration of monoclonal antibody and then rhinovirus binding was measured as described in Example 10. Virus binding is expressed as percent inhibition relative to control binding in the absence of blocking antibody.

FIG. 4 shows circular dichroism spectra of IgG and ICAM-1 proteins. (A) Monoclonal antibody c92.5 IgG; (B) ICAM-1; (C) tICAM(453); (D)- tICAM(185). The spectra for c92.5 IgG, tICAM(453), and tICAM(185) were collected in 20 mM sodium phosphate buffer (pH 7.5) and the spectrum for ICAM-1 was collected in 0.1% octylglucoside/150 mM NaCl/10 mM sodium phosphate (pH 7.5). The data were averaged from 5 repetitive scans, buffer-subtracted and smoothed.

FIG. 5 shows inhibition of ICAM-1/LFA-1-mediated cell adhesion by soluble ICAM-1. Jurkat Y (JY) cells were preincubated with various concentrations of tICAM(453) (filled circles) or tICAM(185) (open squares) for 30 min and then allowed to bind to ICAM-1-coated plates for 60 min at 37° C. The binding of JY cells is >90% inhibited by monoclonal antibody c78.4 to ICAM-1 and monoclonal antibody IOT 16 (AMAC Inc., Me.) to LFA-1.

FIG. 6 shows ICAM-1 mutants based on alignment of human (amino acids I-84 of SEQ. ID NO.1) and murine ICAM-1 domain 1 sequences. Only mouse residues which differ from the human sequence are indicated. (REAF, SEQ ID NO:9, KEDLS, SEQ ID NO:35, SATI, SEQ ID NO:36;KEDL, SEQ DI NO:13) A single gap denoted by the asterisk has been introduced in the mouse sequence to allow the best alignment. Dashed lines below the alignment indicate the predicted positions of beta strands A to F from the model proposed by Giranda et al., Proteins (1990) 7:227–233. The lower part of the figure shows the mutations which were introduced within domain I. A dash in the mutant sequence indicates the position of a conserved residue which was not altered.

FIG. 7 shows rhinovirus binding to chimeric and deglycosylated forms of ICAM-1 expressed in COS cells. [$^{35}$S]-labelled HRV-3 was bound to transfected COS cell monolayers as described in Example 10. Values are expressed as percent specific binding compared to the wild-type ICAM-1 control in the same experiment and were determined from measurements of binding in triplicate. Standard errors (n=3) were less than 10% of the mean value in each case. Virus binding to mouse ICAM-1 was measured using the FT16.I1 transfectant. The ICAM-1 mutant D2Gly- contains Gln residues in place of the four glycosylated Asn residues in domain II.

FIG. 8 shows monoclonal antibody binding to ICAM-1 mutants. Mutants were transfected into COS cells and analyzed by flow cytometry with Mabs c78.4A, c78.5A, and CL203. (A) Staining of COS cells transfected with wild-type ICAM-1 CDNA and an L-cell transfectant expressing murine ICAM-1, using the mouse ICAM-1 antibody 3E5 in place of CL203. (B) Staining of mutants which affect the binding of c78.4A and c78.5A. (C) The binding of c78.4A and (D) of c78.5A to each mutant is expressed as the percentage of cells staining above background compared to staining of the same cell population with the control antibody CL203 TSVS, SEQ ID NO:6; VSIH, SEQ ID NO:7; SKVI, SEQ ID NO:8; REAF, SEQ ID NO:9; LVTCST, SEQ ID NO:10; QVNCSS, SEQ ID NO:11; DQPK, SEQ ID NO:12; KEDL, SEQ ID NO:13;LLGI, SEQ ID NO:5; KELL.

FIG. 9 shows monoclonal antibody reactivity with human/mouse ICAM-1 chimeras. (A) The human/mouse chimeras hm88, hm185, and hm286 consist of human ICAM-1 domain I, domains I and II, and domains I, II, and III respectively (shaded) linked to the corresponding C-terminal fragment of mouse ICAM-1. (B) COS cells were transfected with chimeric cDNAs and analyzed by fluorescent antibody cell sorting (FACS) 48 hours after transfection. Antibody binding is expressed as the percentage of cells showing specific fluorescence above background levels. For antibody binding to mouse ICAM-1, a stable L-cell transfectant FT16.I1 expressing mouse ICAM-1 was used. "ND" indicates the analysis was not performed.

FIG. 10 shows rhinovirus binding to COS cells transfected with ICAM-1 mutants. [$^{35}$S]-labelled HRV-3 was bound to transfected COS cell monolayers and percent specific binding relative to the wild-type control was determined as described in Example 10. Values were determined from triplicate wells, and standard errors were less than 10% of the mean. Bars denote the standard error determined from two independent transfection and binding experiments. Flow cytometry was performed in parallel with virus binding to ensure that the expression level of each mutant was in the range which allows maximal binding of virus to wild-type ICAM-1 TSVS, SEQ ID NO:6; VSIH, SEQ ID NO:7; SKVI, SEQ ID NO:8; REAF, SEQ ID NO:9; LVTCST, SEQ ID NO:10; QVNCSS, SEQ ID NO:11; DQPK, SEQ ID NO:12; KEDL, SEQ ID NO:13; LLGI, SEQ ID NO:5; SLGL, SEQ ID NO:14; KELL, SEQ ID NO:3; DELE, SEQ ID NO:15; LPGN, SEQ ID NO:16; ESGP, SEQ ID NO: 17; RKVY, SEQ ID NO:18; WKLF, SEQ ID NO:19; NVQEDSQ, SEQ ID NO:20; EIGEDSS, SEQ ID NO:21; MCYS, SEQ ID NO:22; and LCFE, SEQ ID NO:23.

DETAILED DESCRIPTION

Figure 1:
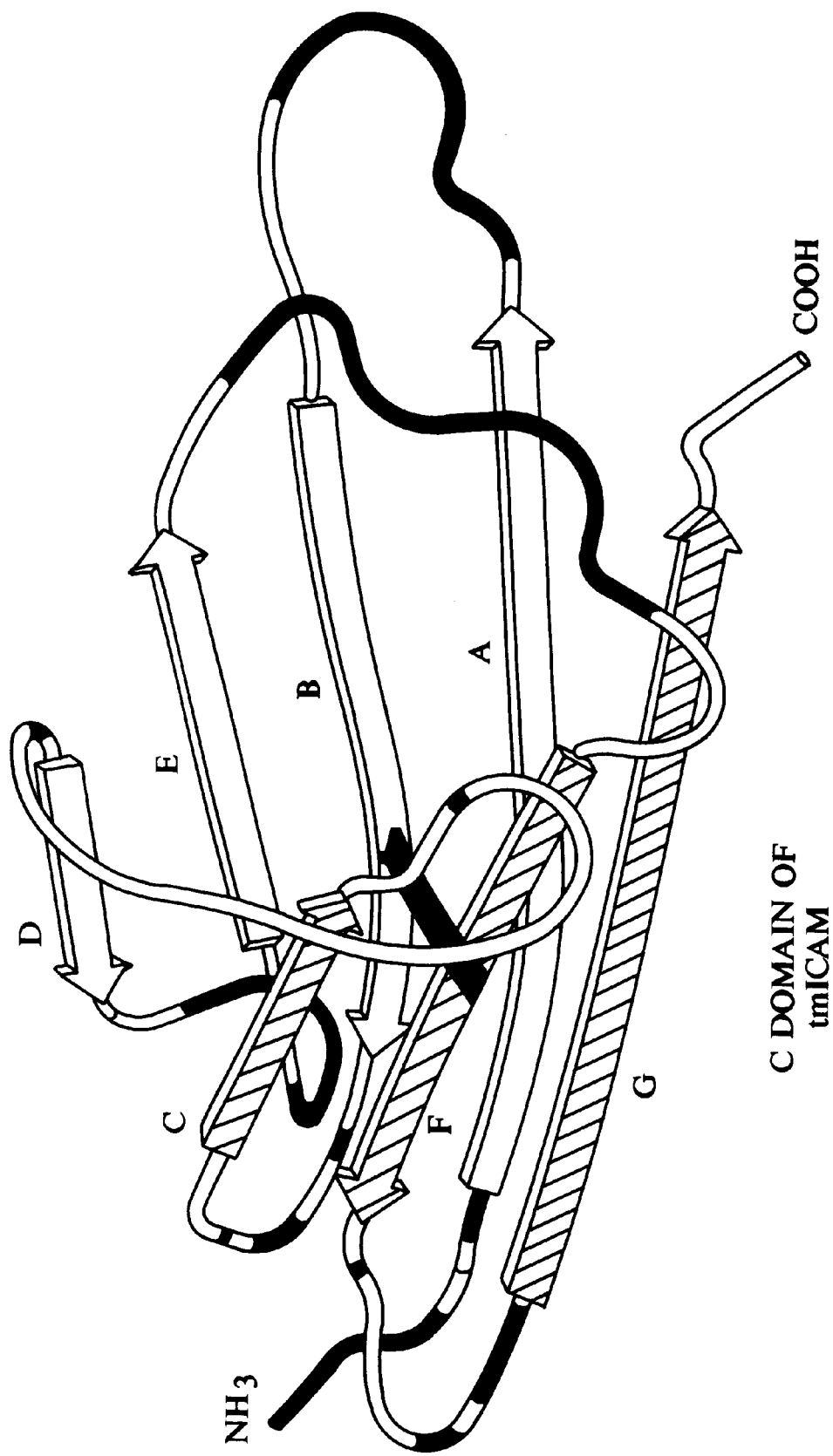

As used herein, the following abbreviations and terms include, but are not necessarily limited to, the following definitions:

| Abbreviation | Definition |
| --- | --- |
| ICAM | Intercellular adhesion molecule - may be used to denote both full length (transmembrane) and truncated forms of the protein. |
| ICAM-1 | Intercellular adhesion molecule-1, also known as tmICAM-1 and HRR; denoting the full- length transmembrane protein. |
| tmICAM-1 | Transmembrane intercellular adhesion molecule-1, also known as ICAM-1 and HRR; requires, e.g., detergent conditions to be solubilized. |
| HRR | Human rhinovirus receptor, also known as ICAM-1 and tmICAM-1. |
| sICAM-1 | A naturally-occurring soluble truncated form of ICAM-1 having both the hydrophobic transmembrane domain and the carboxyl-terminal cytoplasmic domain of ICAM-1 deleted; consists of amino acids 1-442 of ICAM-1 plus 11 novel amino acids. |
| tICAMs | Truncated intracellular adhesion molecules; soluble non-transmembrane ICAMs lacking the hydrophobic transmembrane domain and the carboxyl-terminal cytoplasmic domain of ICAM-1. |
| tICAM(453) | Truncated form of ICAM comprising the entire extracellular amino-terminal domain of tmICAM (domains I–V, amino acid residues 1–453). |
| tICAM(283) | Truncated form of ICAM comprising domains I, II, and III (amino acid residues 1–283). |
| tICAM(185) | Truncated form of ICAM comprising domains I and II (amino acid residues 1–185). |
| tICAM(88) | Truncated form of ICAM comprising domain I (amino acid residues 1–88). |
| tICAM(89-185) | Truncated form of ICAM comprising domain II (amino acid residues 89–185) |
| tICAM(186-283) | Truncated form of ICAM comprising domain III (amino acid residues 186–283) |
| tICAM(284-385) | Truncated form of ICAM comprising domain IV (amino acid residues 284–385) |
| tICAM(386-453) | Truncated form of ICAM comprising domain V (amino acid residues 386–453) |
| tICAM(75-77) | Truncated form of ICAM comprising amino acid residues 75–77 |
| tICAM(70-72) | Truncated form of ICAM comprising amino acid residues 70–72 |
| tICAM(64-66) | Truncated form of ICAM comprising amino acid residues 64–66. |
| tICAM(40-43) | Truncated form of ICAM comprising amino acid residues 40–43 |
| tICAM(36-38) | Truncated form of ICAM comprising amino acid residues 36–38 |
| tICAM(30-33) | Truncated form of ICAM comprising amino acid residues 30–33 |
| tICAM(26-29) | Truncated form of ICAM comprising amino acid residues 26–29 |

The ICAM-1 terminology has been used although it is now recognized that the terms HRR and ICAM-1 are interchangeable.

The foregoing terms defining specific fragments are intended to include functional derivatives and analogs thereof. Persons skilled in the art will understand that the given boundaries may vary by a few amino acid residues without affecting the function of the given fragment.

"Multimerization" and "multimeric" include, but are not limited to dimerization and dimeric, and include any multimeric configuration of the ICAM-1 molecule, or fragment thereof, that is effective in reducing viral binding and infectivity.

"Transmembrane" generally means forms of the ICAM-1 protein molecule which possess a hydrophobic membrane-spanning sequence and which are membrane-bound.

"Non-transmembrane" generally means soluble forms of the ICAM-1 protein including truncated forms of the protein that, rather than being membrane bound, are secreted into the cell culture medium as soluble proteins, as well as transmembrane forms that have been solubilized from cell membranes by lysing cells in non-ionic detergent.

"Truncated" generally includes any protein form that is less than the full-length transmembrane form of ICAM.

"Form" is generally used herein to distinguish among full-length and partial-length ICAM forms; whereas "configuration" is generally used to distinguish among monomeric, dimeric, and multimeric configurations of possible ICAM forms.

All forms and configurations of the ICAM-1 molecule, whether full length or a fragment thereof, including muteins, whether monomeric or multimeric, may be fully or partially glycosylated, or completely unglycosylated, as long as the molecule remains effective in reducing viral binding and infectivity.

"Ligand" is generally used herein to include anything capable of binding to at least one of any of the forms and configurations of ICAM and includes, but is not limited to, HRV, other viruses that bind to the "major" group human rhinovirus receptor, LFA-1, and *Plasmodium falciparum* (the causative agent of malaria).

"Human rhinovirus" or "HRV" generally includes all human serotypes of human rhinovirus as catalogued in Hamparian, V., et al., Virol. (1987) 159:191–192.

The sequence of amino acid residues in a peptide is designated in accordance with standard nomenclature such as that given in Lehninger's *Biochemistry* (Worth Publishers, N.Y., 1970).

Full-length ICAM-1, also known as human rhinovirus receptor (HRR), is termed transmembrane ICAM (tmICAM-1). The present invention provides non-transmembrane truncated forms of ICAM-1 designated tICAM-1, i.e., ICAM substantially without the carboxyl-terminal cytoplasmic domain and without the hydrophobic transmembrane domain, which are soluble without the addition of a detergent. Non-transmembrane forms of ICAM can include functional derivatives of ICAM and mutein forms of tICAM. Preferred embodiments are tICAM(453), tICAM(283), tICAM(185), tICAM(88), and tICAMs comprising one or more sequences selected from tICAM(89–185), tICAM (186–283), tICAM(284–385), tICAM(386–453) tICAM (75–77), tICAM(70–72), tICAM(64–66), tICAM(40–43), tICAM(36–38), tICAM(30–33), and tICAM(26–29).

The present invention further provides purified and isolated tICAMs, or functional derivatives thereof, substantially free of natural contaminants. tICAMs can be obtained from transfected cells, e.g., CHO cells, and are characterized by being soluble in the absence of nonionic detergents and being the translation product defined by novel DNA oligomers. These products have the advantage of being secreted from cells in a soluble form and of not being immunogenic. These truncated products differ from the natural insoluble product in that the truncated soluble products do not contain the membrane-spanning and cytoplasmic domains present in the insoluble form.

The present invention provides purified and isolated DNA sequences encoding tICAMs as well as host cells encoding said sequences. The nucleotide sequences coding for tICAMs can be contained in vectors, such as plasmids, and the vectors can be introduced into host cells, for example eukaryotic or prokaryotic cells. Examples of suitable eukaryotic cells are mammalian cells, e.g. CHO cells, HEK293S cells, and yeast cells. Examples of suitable prokaryotic cells are, e.g, *E. coli*. Eukaryotic cells are preferred; mammalian cells are particularly preferred.

Also provided by the invention are novel pharmaceutical compositions comprising a pharmaceutically acceptable solvent, diluent, adjuvant or carrier, and as the active ingredient, an effective amount of a polypeptide characterized by having HRV-binding activity and reduction of virus infectivity. tICAMs are preferred.

The invention further provides novel pharmaceutical compositions comprising a pharmaceutically acceptable solvent, diluent, adjuvant or carrier, and as the active ingredient, an effective amount of a polypeptide characterized by having LFA-1-binding activity and reduction of LFA-1 activity.

The present invention further provides methods of recovering a tICAM in substantially pure form comprising the steps of cloning a gene coding for the desired tICAM form in a suitable expression vector in a suitable host. The secretion of a soluble protein eliminates the problems associated with production and purification of an insoluble, cell-membrane-bound protein, since cell lysis is not required and thus continuous culture can be employed along with simplified procedures for purification and isolation of the tICAMs. The protein may be purified using an immunoaffinity column, lectin or wheat germ agglutinin column. Other purification steps may include sizing chromatography, ion chromatography, and gel electrophoresis. The antibody capable of binding to tICAM is selected from antibodies against ICAM-1 (tmICAM or ERR) or fragments thereof.

The present invention includes polyclonal antibodies against tICAM. For a method for producing peptide antisera see Green et al., Cell 28:477–487 (1982).

The invention also includes hybridoma cell lines capable of producing monoclonal antibodies to tICAMs, and the monoclonal antibodies produced by said cell lines.

This invention further includes the therapeutic use of antibodies specifically directed to tICAMs to decrease cell adhesion mediated by ICAM and LFA-1.

Pharmaceutical preparations of proteins, protein fragments, functional domains, and analogs have an application in a plurality of diseases. Since the various forms of ICAM are ligands for both LFA-1 and HRV, they may also be used to block tmICAM interaction with LFA-1, which is critical to many cell adhesion processes involved in the immunological response. This method of inhibition of ICAM-1-mediated adhesion has application in such disease states as inflammation and graft rejection, and for suppression of LFA-1-expressing tumor cells and other processes involving cell adhesion.

A further aspect of the invention is use of fragments, functional domains or analogs of LFA-1 to disrupt interactions between HRR and rhinovirus and thereby treat rhinovirus infections.

This invention further includes a method for substantially reducing infection by HRV of the major receptor group, comprising the step of contacting the virus with tICAM-1 or a functional derivative thereof.

This invention further includes a method for substantially reducing infection by other pathogens of the major HRR group, e.g., Coxsackie virus and *Plasmodium falciparum*, comprising the step of contacting the pathogen with one or more tICAMs or functional derivatives thereof.

The invention further comprises a method for enhancing the binding of a tICAM to a ligand, said improvement comprising the steps of presenting said compound in a form and configuration to said ligand wherein binding of said compound to said ligand is enhanced. Multimeric configurations are preferred.

The invention further comprises a method of treating inflammation, said method comprising inhibiting interaction of ICAM-1 with LFA-1. by contacting ICAM-containing cells with inactivated human rhinovirus.

The invention further comprises a method for substantially reducing infection by picornaviruses, comprising contacting viruses of the picornavirus family with one or more adhesion proteins selected from the group consisting of intercellular adhesion molecule-1 and myelin-associated glycoprotein, and mixtures thereof.

The invention further comprises a method of inhibiting binding of monoclonal antibody c78.4A to an ICAM, said method comprising altering one or more of the following moieties in said ICAM amino acid sequence: Lys-40, Leu-43, Lys-40/Glu-41/Leu-42/Leu-43 [SEQ ID NO:3] .Mutations are preferred in which at least one of the following changing is made: Lys-40 to Asp; Leu-43 to Glu; Lys-40/Glu41/Leu-42/Leu-43 [SEQ ID NO:3] to Asp-40/Glu-41/Leu-42/Glu-43 [SEQ ID NO: 15].

The invention further comprises a method of inhibiting binding of monoclonal antibody c78.5A to an ICAM, said method comprising altering one or more of the following moieties in said ICAM amino acid sequence: Asp-71, Gly-72, Pro-70/Asp-71/Gly-72, Asp-26/Gln-27/Pro-28/Lys-29 [SEQ ID NO:4]. Mutations are preferred in which at least one of the following changes is made: Asp-71 to Gly; Pro-70/Asp-71/Gly-72 to Gly-70/Thr-71/Val-72; Asp-26/Gln-27/Pro-28/Lys-29 [SEQ ID NO:4] to Lys-26/Glu-27/Asp-28/Leu-29 [SEQ ID NO:13].

The invention further comprises a method of inhibiting binding of human rhinoviruses to an ICAM, said method comprising altering one or more of the following moieties in said ICAM amino acid sequence: Met-64/Cys-65/Tyr-66, Lys-40, Leu-43, Asp-71, Pro-70/Asp-72/Gly-73. Asp-26/Gln-27/Pro-28/Lys-29 [SEQ ID NO:4], Asp-71/Gly-72, Leu-30/Leu-31/Gly-32/Ile-33 [SEQ ID NO:5, Thr-75/Ala-76/Lys-77. Mutations are preferred in which at least one of the following changes is made: Met-64/Cys-65/Tyr-66 to Leu-64/Cys-65/Phe-66; Lys-40 to Asp; Leu-43 to Glu; Asp-71 to Gly; Pro-70/Asp-72/Gly-73 to Gly-70/Thr-71/Val/72; Asp-26/Gln-27/Pro-28/Lys-29 [SEQ ID NO:4 ] to Lys-26/Glu-27/Asp-28/Leu-29 [SEQ ID NO:13]; Asp-71/Gly-72 to Thr-71/Val-72; Leu-30/Leu-31/Gly-32/Ile-33 [SEQ ID NO:5] to Ser-30/Leu-31/Gly-32/Leu-33 [SEQ ID NO:14]; Thr-75/Ala-76/Lys-77 to Ser-75/Ala-76/Ser-77.

The invention further comprises a method of improving binding of human rhinovirus to an ICAM, said method comprising altering one or more -of the following moieties in said ICAM amino acid sequence: Pro-36, Leu-37, Pro-38. Mutations are preferred in which Pro-36/Leu-37/Pro-38 is changed to Gln-36/Trp-37/Leu-38.

The following examples describe preparation and characterization of representative compounds of the present invention and representative compositions containing said compounds. As used hereinabove and below unless expressly stated to the contrary, all temperatures and temperature ranges refer to the centigrade system; the term percent or (%) refers to weight percent; and the term mole and moles refer to gram moles.

EXAMPLE 1

Growth, Purification and Assay of Rhinoviruses

Rhinoviruses were grown, purified, and assayed essentially as described in Abraham et al., J. Virol. (1984) 51:340 and Greve et al., Cell, (1989) 56:839. The serotypes chosen for these studies include HRV14, the standard in the field, and HRV3, which has an approximately 10-fold higher affinity for ICAM than does HRV14. HRV2, which binds to the "minor" receptor rather than the "manor" receptor, was used as a negative control.

Rhinoviruses HRV2, HRV3, and HRV14 were obtained from the American Type Culture Collection, plaque purified, and isolated from lysates of infected HeLa-S3 cells. Purified rhinovirus was prepared by polyethylene glycol precipitation and sucrose density gradient sedimentation. Viral purity was assessed by SDS-PAGE analysis of capsid proteins and by electron microscopy. Infectivity was quantified by a limiting-dilution infectivity assay scoring for cytopathic effect,, essentially as described by Minor, P. D., "Growth, assay and purification of picornaviruses," in *Virology: A Practical Approach,* B. W. J. May, ed. (Oxford, IRL Press, 1985), pp. 25–41.

EXAMPLE 2

Production and Isolation of Monoclonal Antibodies to ICAM-1

BALB/cByJ female mice were immunized by intraperitoneal injection of $10^7$ intact HeLa cells in 0.5 ml of phosphate-buffered saline (PBS) three times at 3-week intervals. Two weeks later the mice were bled and aliquots of serum were tested for protective effects against HRV14 infection of HeLa cells. Positive mice were boosted by a final injection of $10^7$ HeLa cells, and 3 days later spleen cells were fused to P3X63-Ag8.653 myeloma cells [Galfre, et al., Nature (1977) 266:550–552] to produce a total of approximately 700 hybridoma-containing wells. Each well was tested by incubating $3 \times 10^4$ HeLa cells in 96-well plates with 100 ul of supernatant for 1 hour at 37° C.; the cells were then washed with PBS, and a sufficient amount of HRV14 was added to give complete cytopathic effect in 24–36 hours. Wells that were positive (protected from infection) were scored at 36 hours.

Cells were removed from wells which scored positive in the first screen and cloned by limiting dilution in 96-well microtiter plates. Supernatants from these wells were tested in the cell protection assay and positive wells were again identified. Further clonings were performed until all of the hybridoma-containing wells were positive indicating a clonal population had been obtained. Four cloned cell lines, and their corresponding antibodies, were obtained and were designated c78.1A, c78.2A, c78.4A, c78.5A. An additional two cell lines were obtained by hyperimmunizing mice with L-cells transfected with human genomic DNA comprising HRR and were designated c92.1A and c92.5A.

C92.1A was deposited on Nov. 19, 1987 with the American Type Culture Collection, 12301 Parklawn Drive, Rockville, Md. 20852 and was designated HB 9594.

EXAMPLE 3

Antibody Binding to ICAM-1

Blocking studies with the panel of six monoclonal antibodies to ICAM-1 (all of which protect HeLa cells from infection by human rhinovirus of the major receptor group by binding to ICAM-1) indicated that there are two distinct epitopes defined by these antibodies, one defined by c78.4 (containing c78.1, c78.2, c92.1, and c92.5), and the other by c78.5.

Competitive binding of [125I]-labelled antibody and [35S]-labelled rhinovirus to HeLa cells was measured in the presence or absence of an excess (1 µg/ml) of cold competitor antibody preincubated with the cells for 30 min. Cell adhesion was measured by the binding of the JY cell line to ICAM-1 coated plastic. These antibodies could be assigned into two groups which recognize distinct epitopes:

TABLE I

| Blocking MAb | Percent binding | | | |
|---|---|---|---|---|
| | [$^{125}$I]c78.4A | [$^{125}$I]c78.5A | [$^{35}$I]HRV-3 | JY cells |
| None | 100 | 100 | 100 | 100 |
| c78.4A | 2 | 101 | 6 | 2 |
| c78.5A | 98 | 7 | 9 | 3 |

Figure 3:
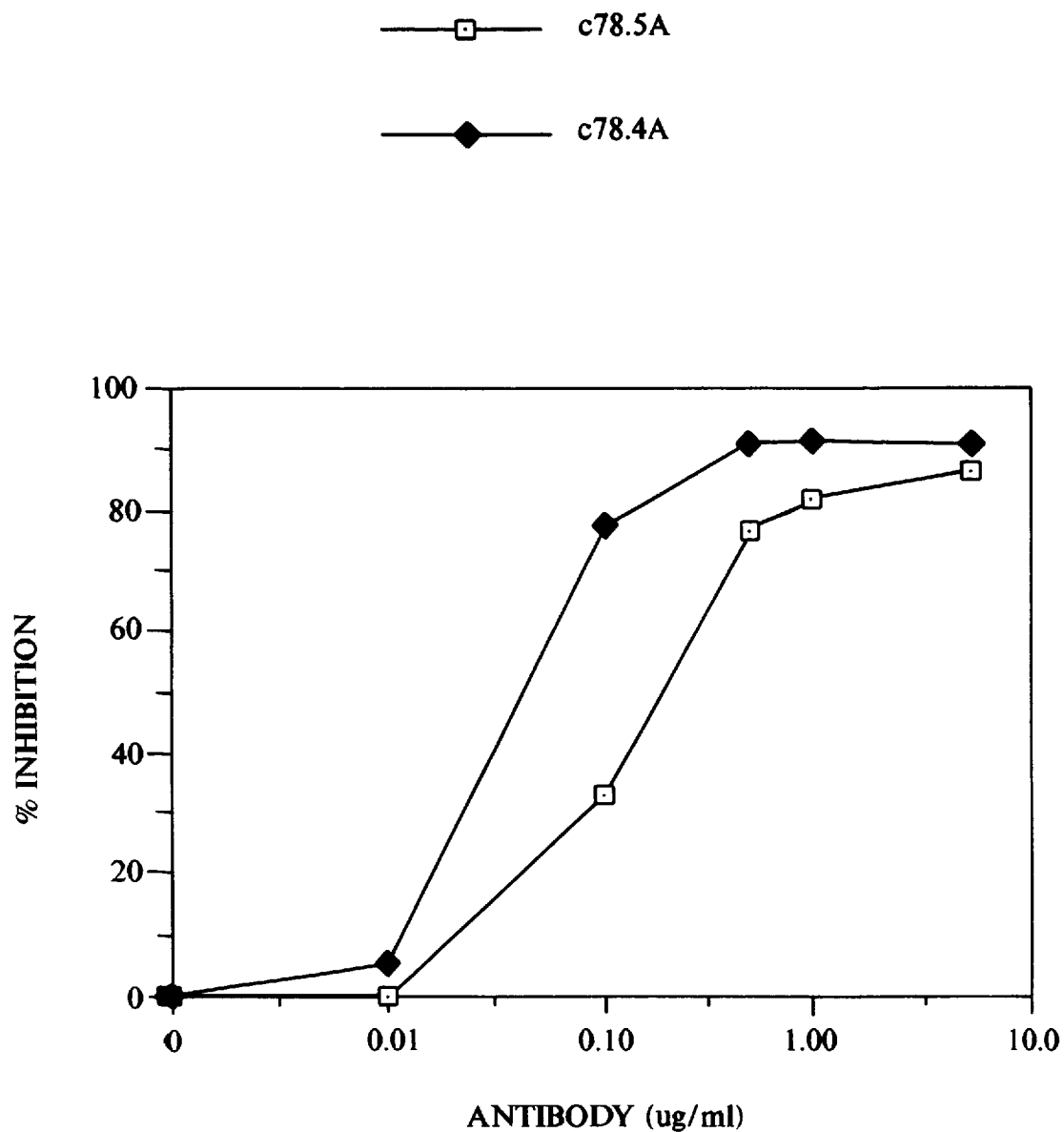

The epitope recognized by c78.4A is shared by 6 of the 7 antibodies examined, with c78.5A being the sole representative of its group. Table I also shows that in addition to the inhibition of HRV binding to cells, both of these antibodies inhibit the LFA-1 dependent adhesion of JY cells to ICAM-1 coated plastic. The antibodies both recognize conformation dependent epitopes since they immunoprecipitate native ICAM-1, but fail to react with the denatured protein on Western blots (data not shown). We have compared the virus blocking activities of the two antibodies by measuring the binding of [$^{35}$S]-labelled HRV-3 to HeLa cell monolayers preincubated with a range of antibody concentrations (FIG. 3). Antibody c78.4A is more efficient in blocking virus attachment with 50% inhibition of binding at 40 ng/ml compared to 200 ng/ml for c78.5A.

For antibody competition experiments, purified monoclonal antibodies were radiolabelled with [$^{125}$I]-Bolton-Hunter reagent to a specific activity of approximately 2×10$^6$ cpm/ug. HeLa cells (10$^6$ cells in 0.1 ml DMEM/2% fetal calf serum (FCS)/10 mM HEPES pH 7.0) were pre-incubated at 4° C. with 3 ug/ml unlabeled monoclonal antibody. 30 ng of $^{125}$I monoclonal antibody was added and after an additional 60 minutes the cells were pelleted by spinning through 1 ml of 5% Ficoll/PBS; the cells were then washed with PBS and bound radioactivity determined.

EXAMPLE 4
Construction of tICAM cDNAs

Figure 2A:
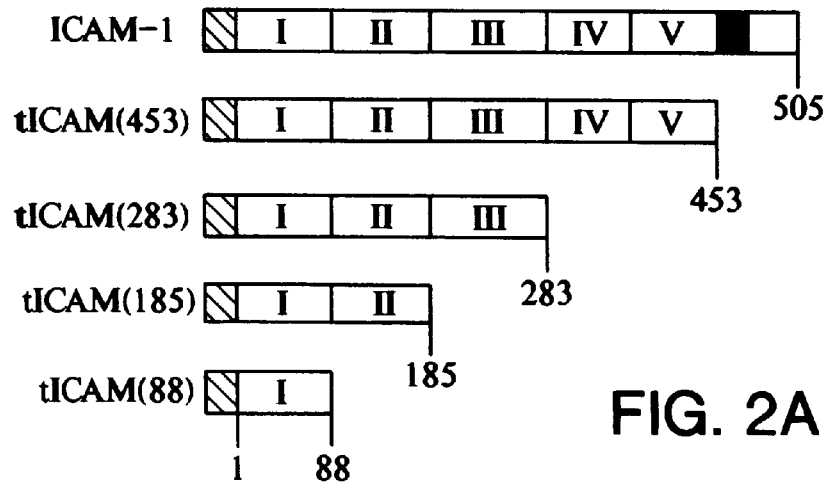

ICAM-1 cDNAs encoding soluble truncated forms were constructed by using polymerase chain reaction (PCR) [Saiki, et al., Science (1985) 230:1350–54] to insert stop codons within the reading frame of the ICAM-1 cDNA pHRR-2, [Greve, et al., Cell (1989) 56:839–847]. The plasmid DNA was digested with EcoR1 to excise the ICAM-1 insert and treated with alkaline phosphatase to prevent recircularization of the vector in subsequent ligation steps. 10 ng of template DNA was subjected to 10 cycles of PCR amplification using the 5' oligonucleotide primer GGAATTCAAGCTTCTCAGCCTCGCTATG-GCTCCCAGCAGCCCCCGGCCC [SEQ ID NO:24] and the 3' oligonucleotide primers GGAATTCCTGCAGT-CACTCATACCGGGGGGAGAGCACATT [SEQ ID NO:25] [for tICAM (453)], TTCTAGAGGATCCT-CAAAAGCTGTAGATGGTCACTGTCTG [SEQ ID NO:26] [for tICAM (283)], TTCTAGAGGATCCT-CAAAAGGTCTGGAGCTGGTAGGGGG [SEQ ID NO:27] [for tICAM (185)], and TTCTAGAGGATCCT-CACCGTTCTGGAGTCCAGTACACGG [SEQ ID NO:28 [for tICAM(88)]. The PCR reaction products were digested with EcoR1 [tICAM(453)] or EcoR1 and BAMH1 [tICAM (283), tICAM(185), and tICAM(88)] and cloned into the polylinker site of Bluescript SK+ (Stratagene). In this manner, stop codons were inserted immediately before the first residue of the transmembrane domain, at the predicted ends of domains I+II+III, domains I+II, and domain I to produce a series of progressively truncated proteins (FIG. 2A). Clones containing the desired inserts were verified by restriction analysis and DNA sequencing.

The inserts were excised by digestion with HindIII and XbaI, inserted into the expression vector CDM8 [Seed, B., Nature (1987) 239:840–42], transfected into COS cells for transient expression, and co-transfected with pSV2-DHFR into CHO cells for establishment of stable cell lines. For transient expression, COS cells were transfected by the DEAE-dextran method [Kingston, R. E., in *Current Protocols in Molecular Biology*, F. M. Ausubel, R. Brent, R. E. Kingston, D. D. Moore, J. G. Seidman, J. A. Smith, and K. Struhl, eds., pp. 9.0.1–6] and pulse-labeled 72 hours after transfection with [$^{35}$S]-cysteine for 18 hours; culture supernatants were then immunoprecipitated with c78.4 IgG-Sepharose and analyzed by SDS-PAGE [Greve, et al., Cell (1–989) 56:839–847]. Stable CHO transfectants were obtained by cotransfection of ICAM-1 cDNAs with pSV2-DHFR into dihydrofolate reductase-deficient CHO cells by the calcium phosphate method or by electroporation [Bebbington and Hentschel, in *DNA Cloning—A Practical Approach*, Vol. 3, D. M. Glover, ed. (IRL Press, Oxford, 1987), pp. 163–188].

Figure 2B:
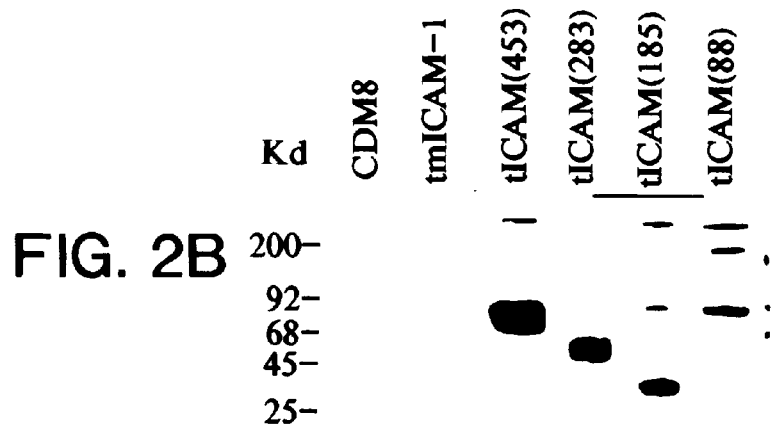

This experiment indicated that the entire extracellular domain [tICAM(453)] and the two N-terminal domains [tICAM(185)] were efficiently secreted from transfected COS cells as species of 80 kD and 43 kD, respectively (FIG. 2B). The expression of domains I+II+III [tICAM(283)] was approximately 10-fold lower than the above-mentioned fragments and the secreted protein was more heterogeneous in mobility on SDS-PAGE. Expression of domain I [tICAM (88)] could not be detected in COS cells, and alternative constructs in which the stop codon was shifted to several sites N- and C-terminal to residue 88 also failed to produce detectable amounts of protein.

Transfected cells were cloned and individual clones secreting ICAM-1 protein were identified by radioimmunoassay of culture supernatants. The expression of tICAMs was monitored by immunoprecipitation of [$^{35}$S]-cysteine-labeled culture supernatants with monoclonal or polyclonal antisera followed by SDS-PAGE. Two monoclonal antibodies, c92.5 (which recognizes the same epitope as c78.4) and c78.5. define two distinct conformational epitopes on ICAM-1. These two antibodies were utilized in an RIA for soluble ICAM-1. c92.5 IgG was absorbed onto Immulon-4 microtiter plates, the plates blocked with 10 mg/ml BSA, and the plates incubated with tICAM-containing samples. The plates were then washed, incubated with $^{125}$I-c78.5 IgG, and the bound radioactivity determined. The concentration of tICAM was determined by comparison to a standard curve of purified ICAM-1.

Cell lines secreting tICAM(453) (CT.2A) and tICAM (185) (CD12.1A) were selected for further study and were subjected to gene amplification in methotrexate-containing media [Bebbington et al., supra]. In order to obtain sufficient quantities of protein for functional and structural studies, CHO cell transfectants were cloned and subjected to stepwise gene amplification in increasing concentrations of methotrexate. A clone derived from CT.2A (resistant to 100 nM methotrexate) and a clone derived from CD12.1A (resistant to 1 μM methotrexate) were used for purification of soluble truncated proteins.

Figure 2C:
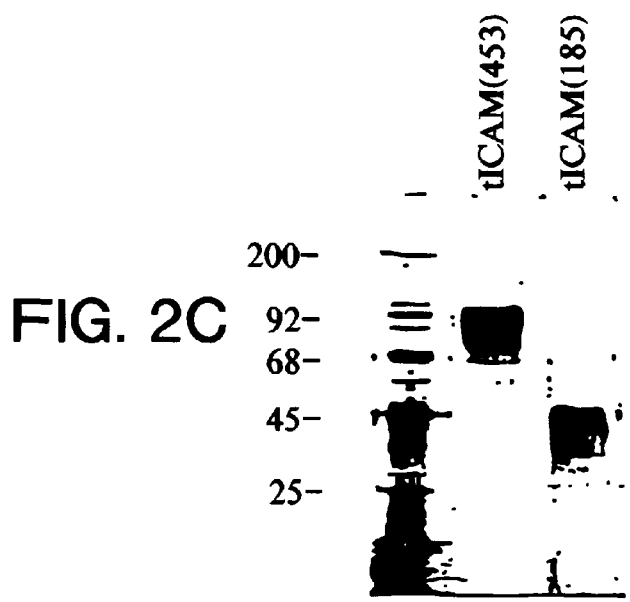

This resulted in the derivation of cell lines secreting 1.5 μg/ml of tICAM(453) and 1.0 μg/ml of tICAM(185). A stable cell line expressing tICAM(283) was not obtained, perhaps because the low level of secretion was at the limit of sensitivity of the immunoassay. The cells were adapted to serum-free media and the secreted ICAM-1 proteins purified to homogeneity from culture supernatants (FIG. 2C).

tICAM(453) and tICAM(185) were purified from culture supernatants of their respective CHO transfectant cell lines by monoclonal affinity chromatography as described in Greve et al., Cell (1989) 56:839–847, followed by ion exchange chromatography on Mono-Ō [for tICAM(453); absorption in 10 mM Tris (pH 6.0), elution in a 0–0.5M NaCl gradient] or gel filtration on Superose-12 [for tICAM (185)] columns (Pharmacia). Protein was quantified by amino acid analysis and by RIA. Amino acid analysis was performed on an Applied Biosystems Model 420A amino acid analyzer.

EXAMPLE 5

Structure of tICAMs

Immunoprecipitation studies with proteolytic fragments of ICAM-1 and with in vitro translations of truncated ICAM-1 cDNAs indicate that the epitopes for both c78.4-type and c78.5-type monoclonal antibodies are contained within the first Ig-like domain.

In vitro virus-binding studies utilizing radiolabeled tICAM(453) and purified HRV have indicated that tICAM (453) can bind to rhinovirus in solution.

ICAM has been predicted, based on homology to NCAM, to be a member of the immunoglobulin gene superfamily. One would expect that the immunoglobulin-like domains in ICAM would have the basic "immunoglobulin fold", as has been shown for two other members of this family, beta-2-microglobulin and the HLA-A2 alpha-3 domain. This fold consists of a "beta-barrel" conformation consisting of two antiparallel beta-pleated sheets, one composed of three and one composed of four beta strands; a disulfide bond between two cysteine residues (separated by approximately 60 amino acids along the chain) connects the two sheets [Williams, A. F., Immun. Today (1987) 8, 298–303]. Two of the disulfide bonds, those corresponding to domains II (C110–C161) and III (C212–C265), have been experimentally determined by us, providing support for the model. This model for the structure provides a basis for designing unique analogs that mimic the virus-binding site and are useful as receptor blockers. Each pair of antiparallel beta strands in the beta-barrel is linked by a hairpin turn of variable size; such turns or loops that protrude from secondary structures are often found to play roles in recognition of ligands [Lezczynski and Rose, Science (1986) 224:849–855]. Such protruding structures may be of particular interest in the rhinovirus receptor, since the receptor-binding site on the virus capsid is proposed to be in a recessed cavity. Using the sequence of the HRR, such turns and loops can be predicted based on a beta-barrel structure and produced as synthetic peptides with addition of novel cysteine residues at the N- and C-terminus of the peptides; a disulfide bond can then be formed between such residues on the same peptide to close the loop covalently (in contrast to the native protein, wherein the loop would be closed by noncovalent interactions between the adjacent beta-strands). Such peptides would have a conformation more analogous to the conformation in the native protein than a simple linear peptide, suitable for virus-binding activity.

EXAMPLE 6

Hydrodynamic Properties of tICAMs

The values $f_{exp}/f_o$ of truncated ICAM-1 proteins were determined from the apparent Stokes radii ($R_s$) determined by gel filtration on a Superose-12 column calibrated with protein standards (ferritin, 61.0 A; catalase, 52.2 A; bovine serum albumin, 35.5 A; ovalbumin, 30.5 A; and RNase A, 16.4 A) and the calculated molecular weights of the proteins, using the value of M calculated from the core-glycosylated form of the proteins, determined by synthesis in the presence of swainsonin.

$$f_{exp} = 6\pi\eta R_s$$

$f_0$ (frictional coefficient of solvated sphere) was determined from:

$$f_0 = (v_2 + \delta v_1^o/v_2)^{1/3} f_{min}$$

where $f_{min} = 6 \pi\eta(3Mv_2/4 \pi N_o)^{1/3}$ (frictional coefficient of unsolvated sphere)

The following values are assumed: $v_2=0.73$ cm$^3$/g (partial specific volume of protein), $v_1^o=1.0$ cm$^3$/g (partial specific volume of solvent), $d_1=0.35$ g H$_2$O/g protein (solvation of protein), n–0.01 g/(cm.s) (viscosity of solvent), and $v_1^o=1.0$ cm$^3$/g (specific volume of the solvent).

We have examined several of the physical properties of tICAM(453) and tICAM(185). Both proteins were quantitatively immunoprecipitated by two monoclonal antibodies directed against two distinct conformation-dependent epitopes on ICAM-1, indicating that these epitopes were contained within the first two domains and providing evidence that the purified proteins were correctly folded. The frictional ratio, f/f$_0$, the ratio between the observed and calculated frictional coefficients shown below for both tICAM (453) and tICAM (185) indicates that both fragments of ICAM-1 are highly asymmetric and elongated molecules.

| PHYSICAL PROPERTIES OF tICAM(185) and tICAM(453) | | |
|---|---|---|
| | tICAM(185) | tICAM(453) |
| Mr[1] | 27.2 kD | 64.1 kD |
| R$_s$[2] | 39 A | 52 A |
| f/f$_o$[3] | 1.9 | 1.9 |

[1]Calculated for core-glycosylated proteins.
[2]Determined by gel filtration; desialation of the proteins had no effect on the R$_s$ values.
[3]Calculated as described above.

The ratio of experimental and calculated frictional coefficients, f/f$_0$, of both tICAMs indicate highly asymmetric and elonged shapes, and are consistent with the data reported for a species similar to tICAM(453) [Staunton, et al., Cell (1990) 61:243–254]. Proteins belonging to the immunoglobulin supergene family would be expected to have domains with the "immunoglobulin fold" motif, which is basically two opposed sheets of antiparallel beta-strands with connecting loops. In support of the immunoglobulin homology, disulfide mapping studies of ICAM-1 have revealed the existence of intradomain disulfide bonds predicted by the immunoglobulin fold in domains I–IV. This is consistent with the data of Staunton, et al., Cell (1988) 52:925–933 with regard to tICAM(453).

EXAMPLE 7

Circular Dichroism of tCIAMs

Circular dichroism (CD) spectra were recorded on an AVIV model 62DS spectrometer. Protein solutions at approximately 0.5 mg/ml (determined by amino acid analysis in the indicated buffers) were scanned at 20 C in a cell with a 0.1 cm pathlength. Five respective scans (1 nm interval, 1.5 nm bandwidth) were averaged and buffer-subtracted for each spectrum.

Figures 4A, 4B, 4C, 4D:
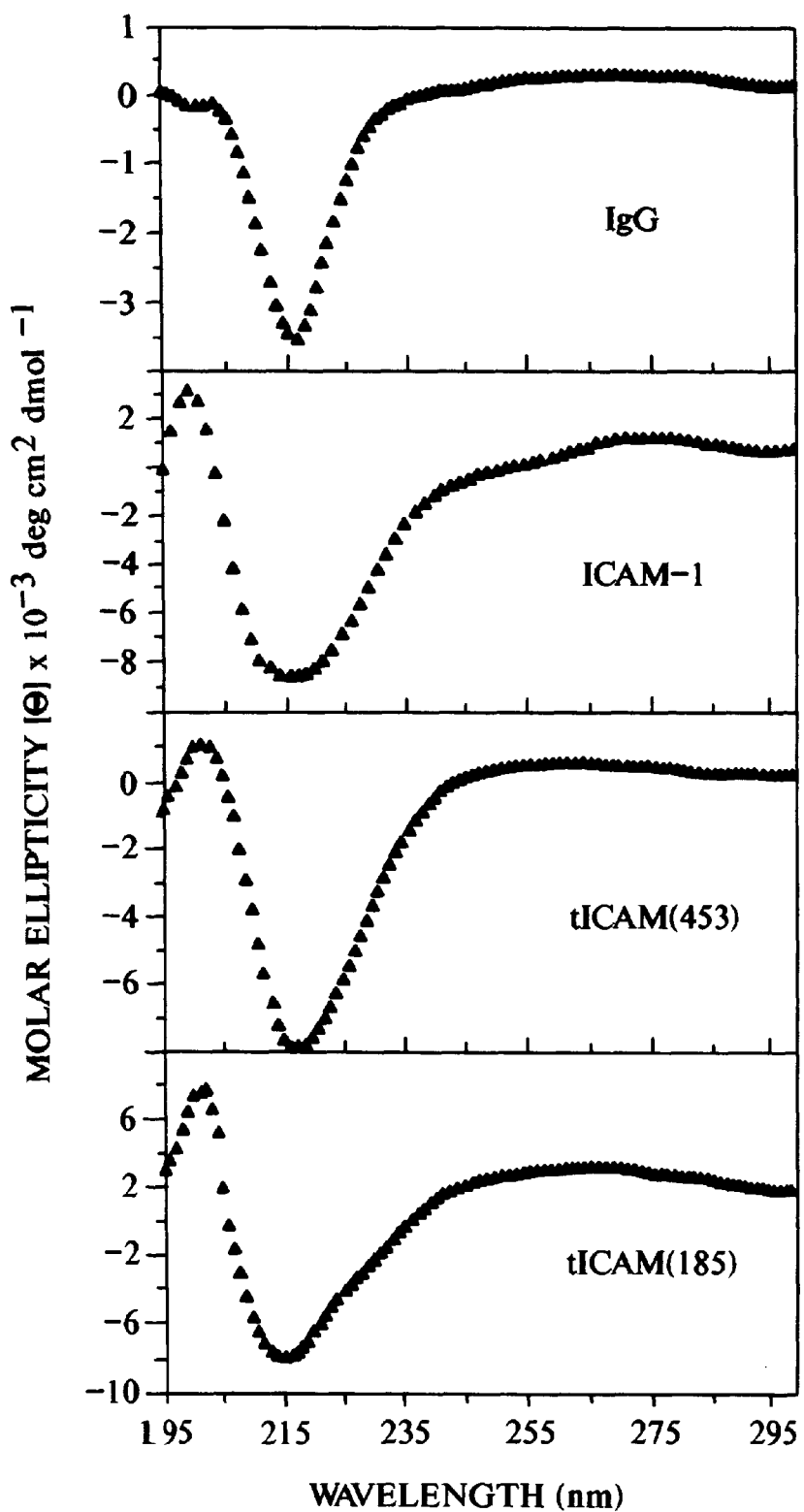

CD spectra were obtained for the soluble forms of ICAM. A single minima at 210–220 nm is indicative of the presence of beta-structure and should be seen in proteins containing immunoglobulin-like domains because of the extensive amount of beta-structure in the "immunoglobulin fold" [Williams, A. F., and A. N. Barclay, Ann. Rev. Immunol. (1988) 6:381–405]. As internal standards, spectra were collected for beta-2-microglobulin and a monoclonal IgG, immunoglobulin-like proteins of known three-dimensional structure [Becker, J. W. and G. N. Reeke, Proc. Natl. Acad. Sci. USA (1985) 82:4225–4229; Bjorkman, P. J., M. A. Saper, B. Samraoui, W. S. Bennett, J. L. Strominger, and D. C. Wiley, Nature (1987) 329:506–512; Amzel, L. M. and R. J. Poljak, Ann. Rev. Biochem. (1979) 48:961–967]. As expected, the spectra of beta-2-microglobulin (not shown) and IgG (FIG. 3A) possessed single major minima at 215 nm and 217 nm, respectively, indicative of extensive amounts of beta-structure. The spectra of the two truncated proteins tICAM(453) and tICAM(185) were similar to each other and to that of ICAM-1 (FIG. 4B; C, and D), with minima at 216–217 nm and a broad shoulder at 225–230 nm, although the shoulder was more prominent with tICAM(185) than tICAM(453). Considered qualitatively, these CD spectra provide evidence that the soluble ICAM-1 proteins are folded and possess considerable amounts of beta-structure. The shoulder at 225–230 nM present in the three tICAMs is not found in the spectra of beta-2-microglobulin and IgG, suggesting the presence of secondary structural features not present in proteins with "classical" immunoglobulin-like domains. The fact that the shoulder at 225–230 is more prominent in tICAM(185) suggests that the secondary structural features detected by this method are localized in the first two domains. These CD data are similar to those reported by Sayre, P. H., R. E. Hussey, H-C Chang, T. L. Ciardelli, and E. L. Rheinherz, "Structural and binding analysis of a two domain extracellular CD2 molecule," J. Exp. Med. (1989) 169:995–1009] for a soluble form of CD2 (which is also thought to be a member of the immunoglobulin supergene family) in that significant amounts of alpha-helix (which is essentially absent from immunoglobulin molecules) was predicted from the CD spectra. When individual domains of ICAM-1 are compared to domains from other members of the immunoglobulin supergene family by the ALIGN program [Dayoff, M. O., W. C. Barker, and L. T. Hunt, Methods in Enzymology (1983) 91:524–545], the similarity is quite limited, with only domains II and III of ICAM-1 having significant scores (above 3 SD; for discussion see Williams, A. F., and A. N. Barclay, Ann. Rev. Immunol. (1988) 6:381–405]. Domain I has a significant score only when compared with domain I from ICAM-2 and vascular cell adhesion molecule-1 (VCAM-1), proteins that are closely related in function. In addition, domain I has a number of unusual features, such as a short distance (44 residues) between intradomain disulfide bonds and the presence of four cysteines instead of the usual two in the B and F beta-strands.

EXAMPLE 8

Radioactive Labeling of tmICAM-1, tICAM(185), and tICAM(453) and Demonstration of Retained Capacity for Binding to Anti-ICAM-1 Monoclonal Antibodies The epitopes reactive with monoclonal antibodies c78.4A and c78.5A are conformationally-dependent epitopes and thus can be used an analytical probes for confirming retention of the native ICAM structure. Known amount of purified ICAM were incubated with c78.4A or c78.5A IgG-Sepharose™ and the fraction of the radioactivity bound determined. These experiments showed that the purified tmICAM-1, tICAM(185), and tICAM(453) completely retained the ability to bind to these monoclonal antibodies.

Transfectants were metabolically labeled with [$^{35}$S]-cysteine, and cell lysates (for transmembrane ICAM) or culture supernatants (for truncated ICAM) were prepared and incubated with c78.4A IgG-Sepharose™ beads. The beads were washed and absorbed proteins were eluted with SDS and analyzed by SDS-PAGE [see Greve, et al., Cell (1989) 56:839–847]. It was found that the isolated proteins were quantitatively bound to the c78.4A and c78.5A Mabs.

Accordingly, the tICAM(185) and tICAM(453) both have retained native ICAM structure.

EXAMPLE 9

Human Rhinovirus Binding Assays of tmICAM and tICAMs

Described below are three binding assays used to assess binding activity of the various forms of ICAM.

A. Pelleting-Assay

[$^{35}$S]-Cysteine-labeled tmICAM-1 or tICAM-was mixed with HRV3 in 100 µl of 10 mM HEPES (pH 7.5), 150 mM NaCl, 1 mM MgCl$_2$, 1 mM CaCl$_2$, 0.1% Triton X-100. The mixture was incubated for 30 minutes at 37° C., cooled on ice, layered on top of a cushion of 200 µl of 10% glycerol, 0.2M triethanolamine (pH 7.5), and centrifuged in a Beckman air-driven centrifuge at 134,000× g for 30 minutes at 4° C. The top 275 µl was removed, and the pellet was analyzed by SDS-PAGE and scintillation counting. Silver-staining of SDS gels of control experiments indicated that essentially all of the HRV3 is pelleted under these conditions and essentially all of the ICAM remains in the supernatant. The results are shown below:

| ICAM | % ICAM Pelleted[1] |
|---|---|
| tmICAM-1 | 11.6% |
| tICAM(453) | 1.0% |
| tICAM(185) | 4.3% |

[1]Average of 4 experiments; these numbers cannot be directly converted into relative affinities.

These data show that both truncated forms of ICAM bind to rhinovirus.

B. Solution Binding Assay

Previous work has demonstrated that detergent solubilized tmICAM-1 can bind to rhinovirus [Greve, et al., Cell (1989) 56:839–847] and that the extracellular domain of ICAM-1 competes for rhinovirus binding to cells [Marlin, et al., Nature (1990) 344:70–72]. To quantitatively compare the virus-binding properties of the soluble ICAM-1 proteins, a solid-phase competition assay was employed. In these experiments, varying concentrations of soluble competitor ICAM-1 proteins were assayed for the ability to compete for the binding of [$^{35}$S]-HRV3 to immobilized ICAM-1; non-ionic detergent (Triton X-100) was included in the buffers so that the different proteins could be compared under identical conditions. First, tmICAM-1 (isolated in the presence of 0.1% octylglucoside instead of Triton X-100) was diluted 10-fold into a Tris/NaCl buffer and allowed to adsorb to the walls of a microtiter plate (Immunlon-4, Dynatech) overnight. Nonspecific binding sites on the plate were then blocked with 10 mg/ml BSA and binding experiments performed in 0.1% Triton X-100/1 mg/ml BSA/10 mM Tris/200 mM NaCl. Approximately 20,000 cpm of [$^{35}$S]-HRV3 were mixed with varying amounts of tmICAM, tICAM(453) or tICAM(185), incubated for 1 hour at 37° C., and then added to wells of the microtiter plates and incubated for 3 hours at 37° C. The plates were washed and the bound radioactivity determined.

As shown below, tmICAM-1 inhibits virus binding half-maximally at low concentrations (0.008 uM) while tICAM (453) and tICAM(185) inhibit at much higher concentrations (3.1 uM and 9.7 uM, respectively; or 350- to almost 1,000-fold higher than tmICAM).

| ICAM | $IC_{50}^1$ |
|---|---|
| tmICAM | 8.0 ± 3.3 nM |
| tICAM (453) | 3.1 ± 1.8 μM |
| tICAM (185) | 9.7 ± 3.2 μM |

[1]Concentration of ICAM-1 protein needed to inhibit [$^{35}$S]-HRV3 binding to ICAM-1-coated microtiter plates by 50%; average of three experiments ± S.D.

These data confirm and extend the earlier observations that tICAM(453) and tICAM(185) do bind to rhinovirus but with lower affinities than does tmICAM-1 and provide evidence-that-the virus-binding site is encompassed within the two N-terminal domains (first 185 residues) of ICAM-1. The $IC_{50}$ value of tICAM(453) is comparable to that of tICAM(185). The small (three-fold) lower $IC_{50}$ of tICAM (185) is reproducible but of unknown significance at present. It has been reported that a mouse-human chimera of transmembrane ICAM-1 in which the first two domains are of human origin is capable of binding rhinovirus as well as human ICAM-1, while a shortened transmembrane form containing only the two N-terminal domains binds rhinovirus at approximately one-tenth the level of full-length ICAM-1 [Staunton, et al., Cell (1990) 61:243–254]. These workers interpret these results as demonstrating that domains I and II are important for rhinovirus binding while the distance from the plane of the membrane determines the efficiency with which the rhinovirus can approach the binding site. The interpretation of these results is limited by the requirement for species-specificity of all possible interactions with the rhinovirus and by the steric limitations of shortened transmembrane molecules. Our results with the soluble ICAM-1 clearly and quantitatively demonstrate that the virus-binding site is contained within the first two N-terminal domains.

C. Dot-Blot Assay

An alternative method of measuring binding activity was utilized in which tmICAM-1, tICAM(453), or tICAM(185) were adsorbed to nitrocellulose filters, the non-specific binding sites on the filters blocked with 10 mg/ml bovine serum albumin (BSA), and radioactive virus or [$^{125}$I]-monoclonal antibody to ICAM-1 incubated with the filter for 60 minutes at 37° C. The filters were washed with buffer and the filters exposed to X-ray film.

The amount of radioactivity bound to the filters was determined by densitometry of the autoradiograms, and the data is expressed as HRV3 binding (in arbitrary units) normalized to the amount of ICAM bound to the blot by a parallel determination of the amount of $^{125}$I-monoclonal antibody c78.4A or c78.5A bound to the ICAM (bound to the blot). The results are shown below:

| Binding of [$^{35}$S]-HRV3 to Immobilized ICAM[1] | | |
|---|---|---|
| ICAM | tICAM (453) | ratio ICAM/tICAM (453) |
| 1.2 ± 1.1 | 0.52 ± 0.45 | 2.3 |

[1]Average of 5 experiments. Data is expressed in arbitrary densitometric units of [$^{35}$S]-HRV3 binding/[$^{125}$I]-anti-ICAM monoclonal antibody binding.

The results from this experiment indicate that under these assay conditions tICAM(453) is capable of binding rhinovirus at levels comparable to those of tmICAM-1 when the amount of virus bound was normalized to the amount of [$^{125}$I]-Mab bound. Further, these results indicate that the tICAM forms are capable of binding to rhinovirus, but that the binding avidity is dependent to some degree upon the configuration of the tICAM. tmICAM-1 may be a small multimer (probably a dimer) and presentation of tICAM in a multimeric form mimics this multimeric configuration.

Evidence supporting this hypothesis comes from quantitative binding studies, in which the ratio of the maximum number of rhinovirus particles and the maximum number of antibody molecules that can be bound to cells is approximately 1.5. This is in contrast to the earlier work of Tomassini, J., et al., (1986) J. Virol. 58:290, which suggested a complex of five molecules needed for binding. Their conclusion was based on an erroneous interpretation of gel filtration data that failed to take into account bound detergent molecules.

EXAMPLE 10

HRV Infectivity Assays

HRVs and [$^{35}$S]-HRV3 was propagated and purified as described in Example 1. All infectivity assays were performed with HeLa-S3 in Dulbecco's Modified Essential Medium/2% fetal calf serum. Assay I: 0.1 ml of dilutions of HRV3 (with $10^4$–$10^{-1}$ pfu/ml) in the presence or the absence of tICAM(185) or tICAM(453) were added to 10 wells of a 96-well microtiter plate containing $2\times10^4$ HeLa cells/well in 0.1 ml. The cultures were incubated for five days at 34° C. and the titer determined from the number of infected wells at the limiting dilution. Assay II: $10^7$ PFU of HRV3 and various concentrations of ICAM-1 in a final volume of 25 μl of 10 mM HEPES (pH 7.5)/150 mM NaCl were incubated for 30 minutes at 37° C., and then serially diluted into culture medium. The virus was then incubated with HeLa cells at $10^6$ cells/ml for 30 minutes at room temperature, plated into 10 wells of a 96-well microtiter plate at $10^5$ cells/well, and then scored for infectivity as described above. Assay III: 0.1 ml of HRV3 (0.1 μg/ml, $10^7$ PFU/ml) was preincubated for 30 minutes at 37° C. with ICAM-1 and then added to wells of a 96-well microtiter dish containing $10^5$ HeLa cells and incubated for 24 hours. The cultures were then scored by staining with crystal violet [Minor, P. D., in *Virology: A practical approach*, B. W. J. Mahy, ed. (IRL Press, Oxford, 1985), pp. 25–40] and determining the optical density at 550 nm. All experiments were performed in triplicate and the results expressed at the concentration of ICAM-1 needed to reduce the $OD_{550}$ by 50%.

The effect of soluble ICAM-1 on HRV infectivity was examined in three different infectivity assays, the first two being limiting dilution determinations and the third being a high multiplicity of infection (MOI) experiment using the same virus concentrations as the virus binding assay in Example 8. In assay I, cells were infected with serial dilutions of HRV3 in the continuous presence of various concentrations of ICAM-1-and the reduction in virus titer determined. As shown below, the $IC_{50}$ of tICAM(185) for neutralization is 8.2 μM, similar to the concentration needed to inhibit virus binding. In contrast, the $IC_{50}$ for neutralization of tICAM(453) is 0.38 μM, 10-fold lower than the concentration needed to block virus-receptor binding:

NEUTRALIZATION OF RHINOVIRUS BY SOLUBLE ICAM-1

| | $IC_{50}$[1] | | |
|---|---|---|---|
| | tICAM(185) | tICAM(453) | tmICAM-1 |
| Assay I (continuous) | 8.2 μM | 0.38 μM | ND |
| Assay II (pretreatment) | <20 μM | <20 μM | 0.03 |
| Assay III (high MOI) | 13.2 μM | 1.2 μM | ND |

[1]Concentration of ICAM-1 protein needed to inhibit HRV3 infectivity by 50%, as described for each assay above.

Thus, the neutralizing activity of tICAM(185) is directly correlated with its effect on virus receptor binding, while tICAM(453) is neutralizing HRV at a considerably lower concentration and is presumably acting by a mechanism other than direct competition for receptor-binding sites on the virus. Assay II consists of preincubating HRV3 with ICAM-1, serially diluting the mixture into culture medium, and then adding the virus to the cells; under these conditions the ICAM-1 is diluted out to negligible concentrations for the actual infection. tICAM(185) and tICAM(453) had essentially no neutralizing activity in this assay at concentrations as high as 20 uM protein, indicating that the effects of the soluble ICAMs on rhinovirus must be reversible. Assay III consists of a single cycle infection at an MOI of 10 in the continuous presence of various concentrations of soluble ICAM-1. Under these conditions tICAM(453) neutralized HRV with an $IC_{50}$ of 1.2 uM, an 11-fold lower concentration than that of tICAM(185). The relative difference in the concentrations of the two proteins needed to neutralize rhinovirus in Assay III is essentially the same as in Assay I, although the absolute concentrations are approximately 3-fold higher, perhaps because of a nonlinear relationship between infectious particles and infected cells under conditions of high MOI.

The neutralization activities of the two soluble ICAM-1 species examined here are intriguing in that they indicate multiple mechanisms of virus neutralization by receptor. The first mechanism, exemplified by tICAM(185), appears to be a simple competitive inhibition of virus-receptor binding by soluble receptor. The second, exemplified by tICAM(453), involves neutralization of virus at a concentration below that necessary to inhibit virus-receptor binding. This disparity between the virus-neutralizing and virus-binding activities of tICAM(453) indicates that steps in virus entry and/or uncoating are affected by this protein. These apparently different mechanisms of virus neutralization may be reflecting different steps in the entry and uncoating process in which the membrane-bound receptor participates in a normal infection. The modes of action of the capsid-binding WIN compounds as revealed by their effects on different rhinovirus serotypes [Pevear et al., J. Virol. (1989) 63:2002–2007], where some serotypes are blocked from binding to the receptor while other serotypes are blocked at an intracellular uncoating step, suggest a similar "hierarchy" of sites at which the infection can be interrupted. Both of the neutralization mechanisms mediated by soluble ICAM-1 are reversible, since neutralization is seen when cells are infected in the continual presence of soluble ICAM but not when the virus is preincubated at comparable concentrations of ICAM-1 followed by dilution of the ICAM-1 to negligible concentrations. During many picornavirus infections, noninfectious "altered" virions can be recovered from cells, presumably as a direct or indirect result of interaction with the receptor [Roesing, T. G., P. A. Toselli, and R. L. Crowell, J. Virol. (1975) 15:654–667; Guttman, N. and D. Baltimore, Virol. (1977) 82:25–36]. The relationship of the receptor-neutralized rhinoviruses to such "altered" virions found in other picornaviruses is unclear at present.

Marlin, et al., Nature (1990) 344:70–72 have reported that the extracellular domain of ICAM-1-neutralized virus at a concentration of ICAM considerably lower than that needed to inhibit virus-receptor binding, although this discrepancy was attributed to differences in virus concentrations between the binding and infectivity assays. Our results, which show a differential effect of the two soluble ICAM-1 proteins even at virus concentrations identical to that in the virus-binding assay indicate that there is a real difference between binding and neutralizing properties of tICAM(453). Possible explanations include: (1) cooperative interactions between ICAM-1 molecules at the surface of the virus leading to more effective virus inactivation, (2) effects of the size of the ICAM-1/rhinovirus complex on virus internalization or uncoating, or (3) interactions of portions of the ICAM-1 molecule other than the two N-terminal domains with the rhinovirus. In an interesting parallel in another system, the soluble CD-4 mediated neutralization of HIV, a nonlinear relationship between soluble CD4 concentration and neutralization at high fractional occupancy of gp 120 molecules was observed, providing evidence for positive cooperativity between virus-bound CD4 molecules [Layne, S. P., M. J. Merges, M, Dembo, J. L. Spouge, and P. L. Nara, Nature (1990) 346:277–279]. While the molecular basis of tICAM (453)-mediated neutralization or its significance to interaction of the rhinovirus with ICAM-1 at the cell surface remains to be determined, it clearly indicates a role for the three domains C-terminal to residue 185.

EXAMPLE 11

Cellular Adhesion Assay

Jurkat Y (JY) cells ($10^7$ cells/ml in 10 mM HEPES pH7.5/150 mM NaCl/1 mM $CaCl_2$/1 mm $MgCl_2$ containing 1 mg/ml BSA) labeled with 10 uCi/ml [$^{35}$S]-cysteine for 18 hours) were preincubated with soluble tICAM-1 or 10 ug/ml indicated monoclonal antibodies for 30 minutes at 37° C. in Dulbecco's Modified Essential Medium/2% fetal calf serum and then added to 96-well Immulon-4 microtiter plates (Dynatech, Vir.) coated with purified ICAM-1. The plates were then incubated for 60 minutes at 37° C., the plates washed three times with media, and then the bound cells quantified by scintillation counting.

Figure 5:
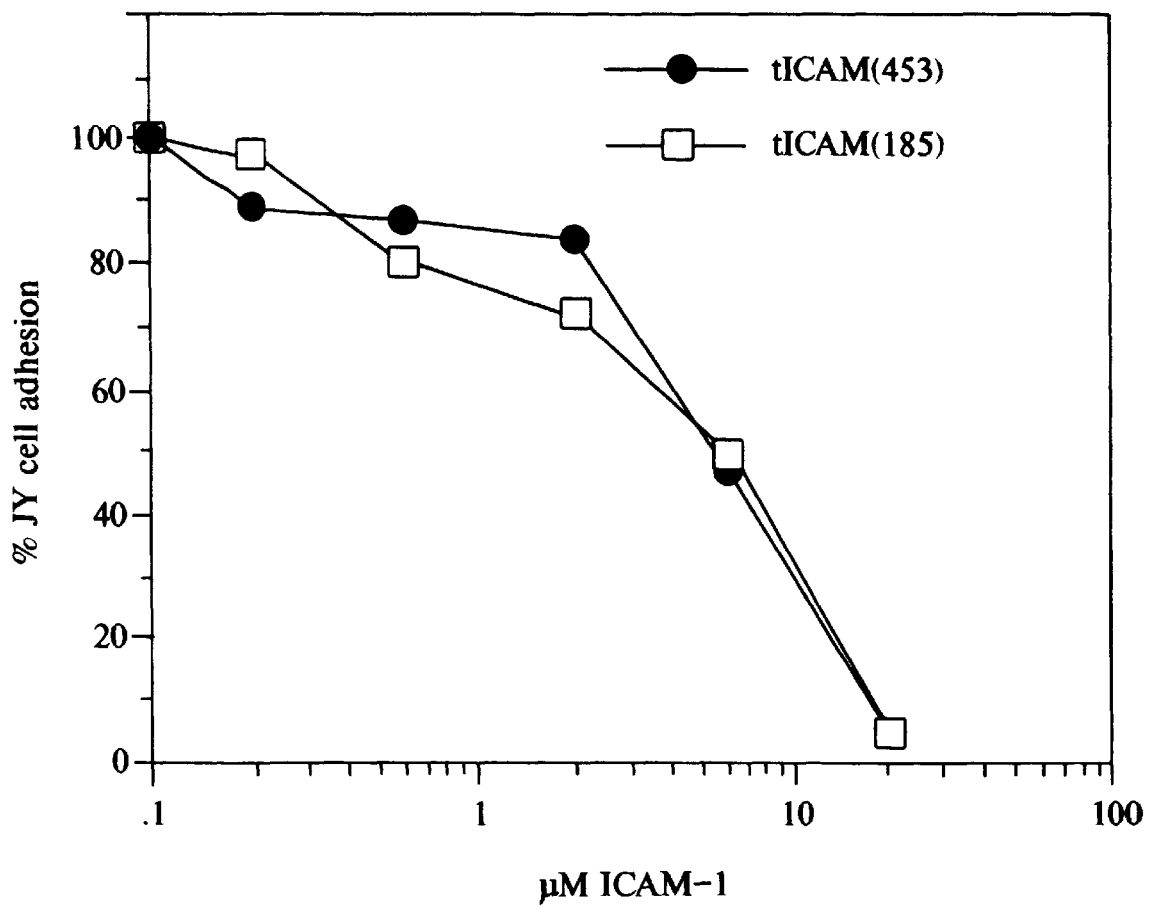

Soluble tICAM molecules were then examined for their ability to inhibit the adhesion of JY lymphoblastoid cells (which express LFA-1) to ICAM-1-coated tissue culture plates. As shown in FIG. 5, tICAM(185) and tICAM(453) both inhibited JY cell binding at identical concentrations of 10 μM, indicating that the LFA-1 binding site is entirely encompassed within the first two domains of ICAM-1.

Previous work has indicated that the two N-terminal domains of ICAM-1 were important in LFA-1 binding, in that site-directed mutagenesis at a number of positions in domains I and II reduce the ability to bind to LFA-1 and a shortened transmembrane molecule containing domains I and II retains one-third of the LFA-1 binding activity of full-length ICAM-1 [Staunton, et al., Cell (1990)

61:243–254]. The relatively high concentration of soluble tICAM-1 needed to inhibit cell adhesion illustrates the fact that ICAM-1/LFA-1-mediated cell adhesion is a cooperative result of multiple weak interactions, as might have been predicted from the strong dependence of ICAM-1/LFA-1 mediated cell adhesion on the density of ICAM-1 [Dustin, M. L. and T. A. Springer, J. Cell Biol. (1989) 107:321–331]. A micromolar dissociation constant has been reported for the CD2/LFA-3 interaction [Sayre. P. H., R. E. Hussey, H-C. Chang, T. L. Ciardelli, and E. L. Rheinherz, "Structural and binding analysis of a two domain extracellular CD2 Molecule," J. Exp. Med. (1989) 169:995–1009], suggesting that low adhesion molecule affinity is a general phenomenon, perhaps to allow for tight regulation of the adhesion process by control of copy number. The identical inhibitory activities of both soluble ICAM-1 proteins toward cell adhesion provide additional evidence that both proteins are correctly folded and underscores the fact that the enhanced neutralizing activity of tICAM(453) relative to tICAM(185) is specific to ICAM-1/rhinovirus interaction.

EXAMPLE 12

Construction of Human/Mouse ICAM-1 Chimeras

We have exploited the fact that the murine homologue of ICAM-1 does not bind rhinoviruses to map regions of human ICAM-1 important for viral attachment. A series of human/mouse chimeras were constructed in order to localize monoclonal antibody and rhinovirus binding determinants within the ICAM-1 structure. Chimeric ICAM-1 molecules were constructed in which human domain I (residues 1–88), domains I and II (residues 1–185), and domains I, II, and III (residues 1–286) were fused to mouse ICAM-1 [Siu, G., S. M. Hedrick, and A. A. Brian, "Isolation of the murine intercellular adhesion molecule-1 (CAM-1) gene", J. Immunol. (1989) 43:3813–3820; Horley, K. J., C. Carpenito, B. Baker, and F. Takei, "Molecular cloning of murine intercellular adhesion molecule-1 (ICAM-1)", EMBO J. (1989) 8:2889–2896] at the corresponding location in the mouse sequence (FIG. 6A).

To construct the human/mouse chimeras hm88 and hm185, PCR amplifications [Saiki, R. K., D. H. Gefland, S. Stoffel, S. J. Scharf, R. Higuchi, G. T. Horn, K. B. Mullis, and H. A. Erlich, "Primer-directed enzymatic amplification of DNA with a thermostable DNA polymerase", Science (1988) 239:487–491] were performed using cloned human and mouse ICAM-1 cDNAs as templates. The murine ICAM-1 cDNA was kindly provided by Dr. A. Brian, UCSD. The PCR primers were used to create novel restriction sites at the boundaries between domains in order to facilitate the gene fusions. The human domains were amplified using a 5' primer GGAATTCAAGCTTCTCAGC-CTCGCTATGGCTCCCAGCAGCCCCCGGCCC [SEQ ID NO:24] which contains EcoRI and HindIII sites followed by 12 bases of 5' untranslated sequence and the first 24 bases of the signal sequence. The human 3' primer for the hm88 construct was GGGATCCGAGCTCCACCCGTTCTG-GAGTCCAGTACAC [SEQ ID NO:29] which contains a BamH1 site followed by 9 bases corresponding to residues 89 to 90 of murine ICAM-1 and 24 bases corresponding to residues 82–89 of human ICAM-1. This oligonucleotide creates a novel SacI site at codons 89 and 90. The mouse 5' primer for the hm88 construct was GGGATCCGAGCTCA-GACCTCTGCCAGCCTGGCAGCAA [SEQ ID NO:30] which contains a BamHI site followed by 30 bases corresponding to residues 89–98 of murine ICAM-1, again creating a SacI site at codons 89 and 90. The 3' primer for all mouse ICAM-1 fragments was GGGATCCTCTAGAT-CAGGGAGGTGGGGCTTGTCCCTT [SEQ ID NO:31] which consist of BamHI and XbaI sites, a stop codon and 21 bases corresponding to the C-terminal 7 residues of ICAM-1. The two fragments were amplified from 10 ng of cDNA plasmid using 10 cycles with 1.5 min extensions at 72° C. The human fragment was digested with HindIII and SacI and the mouse fragment with SacI and XbaI. Following gel purification the fragments were ligated into HindIII/XbaI cut CDM8 vector [Seed, B., "An LFA-3 cDNA encodes a phospholipid-linked membrane protein homologous to its receptor CD2", Nature (1987) 329:840–848]. Appropriate clones were identified by restriction mapping and confirmed by DNA sequencing.

The same approach was used to construct the hm185 fusion using the human 3' primer GGGATCCGCCGGCA-GATCAAAAAGGTCTGGAGCTGGTAGGGGGC [SEQ ID NO:32], and the mouse 5' primer GGGATCCGCCGGC-TACCATCCCAAAGCTCGACACC [SEQ ID NO:33]. These primers create a novel NaeI site allowing the fusion of human residue 185 to murine residue 185. To construct hm286, a naturally-occurring NarI site at the boundary between domains three and four in the human ICAM-1 CDNA was used. A full-length ICAM-1 cDNA clone in CDM8 was digested with NarI and with XbaI which cuts at the 3' end of the insert. The fragment consisting of vector and domains I to III was gel purified and ligated to a mouse fragment amplified using the 5' primer GGGATCCGGCGC-CTGTCCTGACCCTGAGCCAGCTG [SEQ ID NO:34].

EXAMPLE 13

Site-Directed Mutagenesis of Human/Mouse Chimeras

Figure 6:
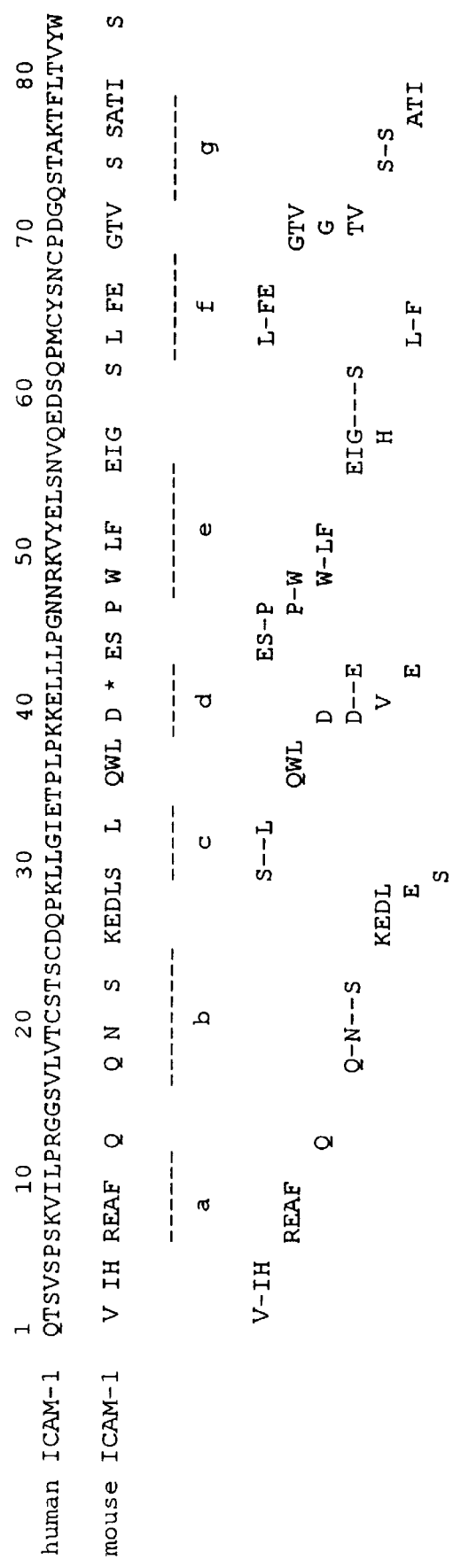

In order to map the monoclonal antibody and rhinovirus binding determinants within domain I, we systematically substituted human residues for corresponding mouse residues throughout this region of the protein. We chose this strategy in an attempt to minimize the introduction of disruptive mutations which might cause global conformational changes. FIG. 6 shows a sequence alignment of human and murine ICAM-1 and illustrates the replacements which were made. A sequence alignment of domain I with IgG consensus sequences based on structural considerations [Giranda et al., Proteins (1990) 7:227–233] was used to predict the positions of beta strands and turns, each of which were changed in a separate mutation to the mouse sequence. Several single amino acid substitutions were also made which replaced human ICAM-1 with residues from murine ICAM-1 or from human ICAM-2 [Staunton, D. E., M. L. Dustin, and T. A. Springer, "Functional cloning of ICAM-2, a cell adhesion ligand for LFA-1 homologous to ICAM-1", Nature (1989) 339:61–64].

ICAM-1 mutants were constructed using single-stranded template DNA of a full-length ICAM-1 CDNA pHRR12–19 in the CDM8 expression vector [Peterson, A. and B. Seed., "Genetic analysis of monoclonal antibody and HIV binding sites on the human lymphocyte antigen CD4", Cell (1988) 54:65–72] and a Mutagene kit (Biorad, Calif.). In most cases codon degeneracy was exploited to introduce a novel restriction site into the mutant to allow for rapid and easy identification of mutant plasmids. All mutants were subsequently verified by DNA sequencing.

EXAMPLE 14

Deglycosylated Mutants of Domain II of ICAM-1

Carbohydrate structures have been shown to be important components of certain viral receptors such as the sialic acid binding specificity of influenza virus [Weis, W., J. H. Brown, S. Cusack, J. C. Paulson, J. J. Skehel, and D. C. Wiley, "Structure of the influenza virus haemagglutinin complexed with its receptor, sialic acid", Nature (1988) 333:426–431]. ICAM-1 contains eight Asn-linked oligosaccharide chains, four of which are in the second domain [Staunton et al., Cell (1988) 52:925–933]. Since the second domain could contribute to the virus binding site, or be in close proximity to areas of contact, it was of interest to determine whether removal of the sugar residues from domain II affects virus binding. This was accomplished by constructing a mutant ICAM-1 molecule in which each of the four glycosylated asparagine residues at positions 103, 118, 156, and 175 were changed to glutamine.

Figure 7:
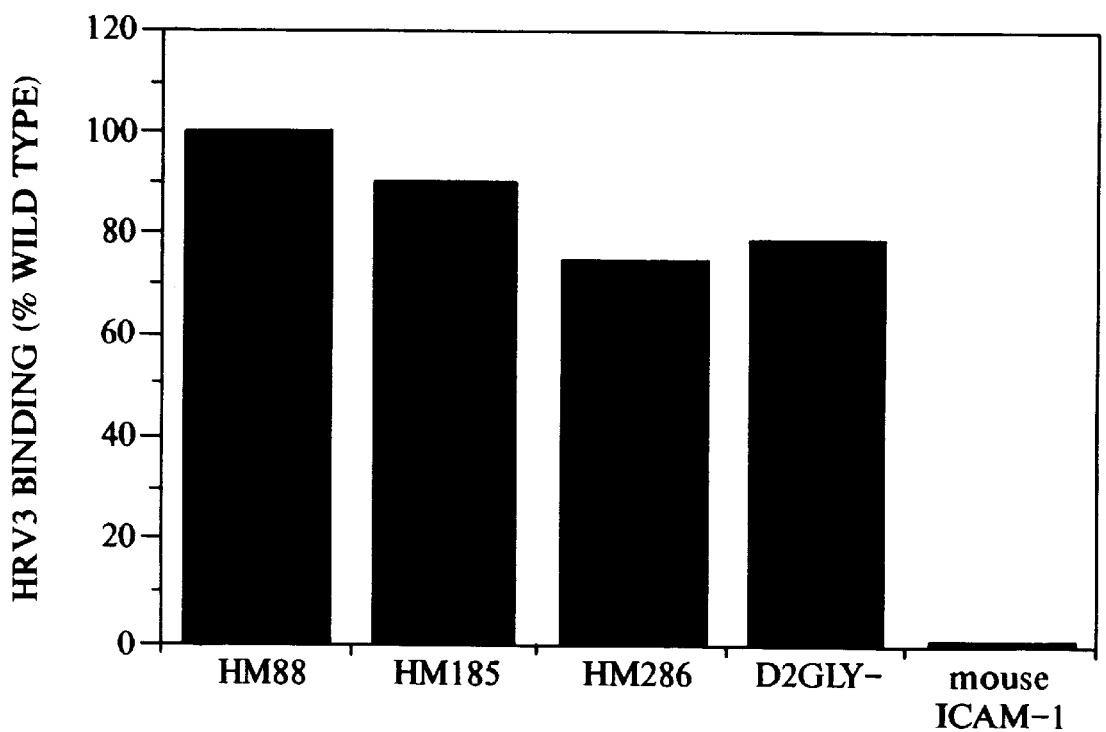
Figure 8A:
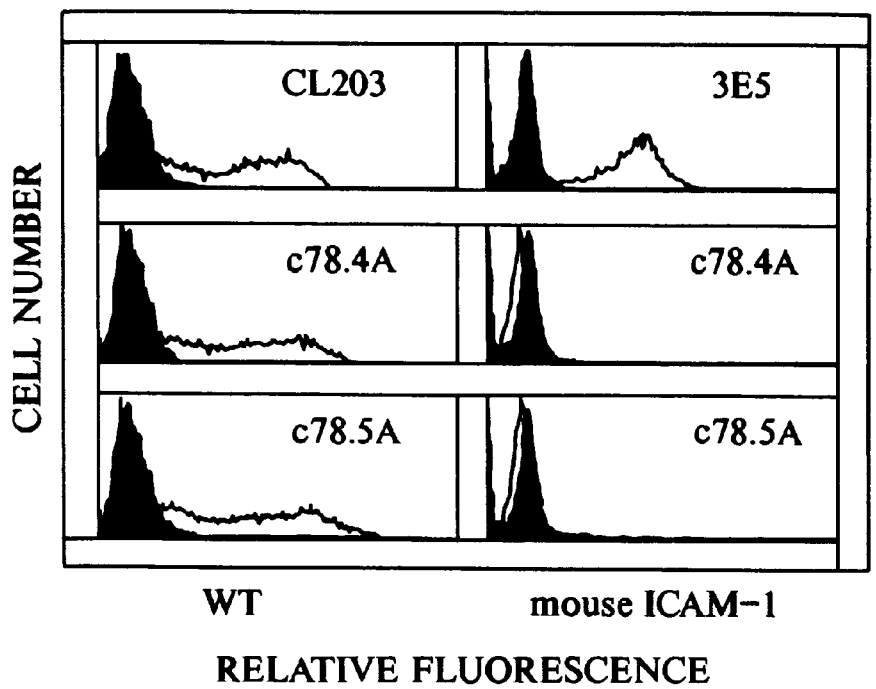
Figure 8B:
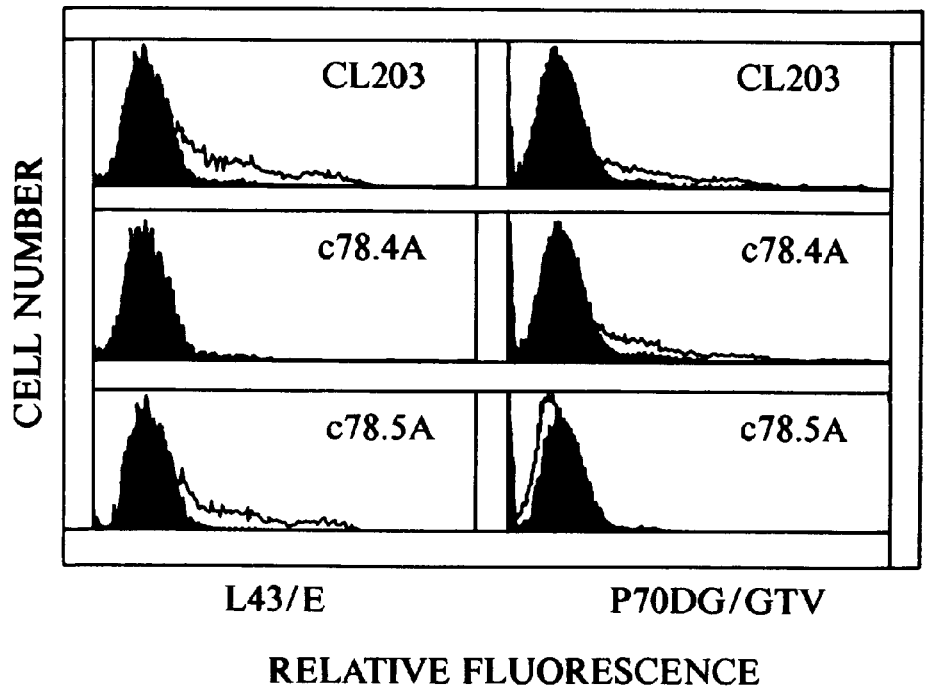
Figure 8C:
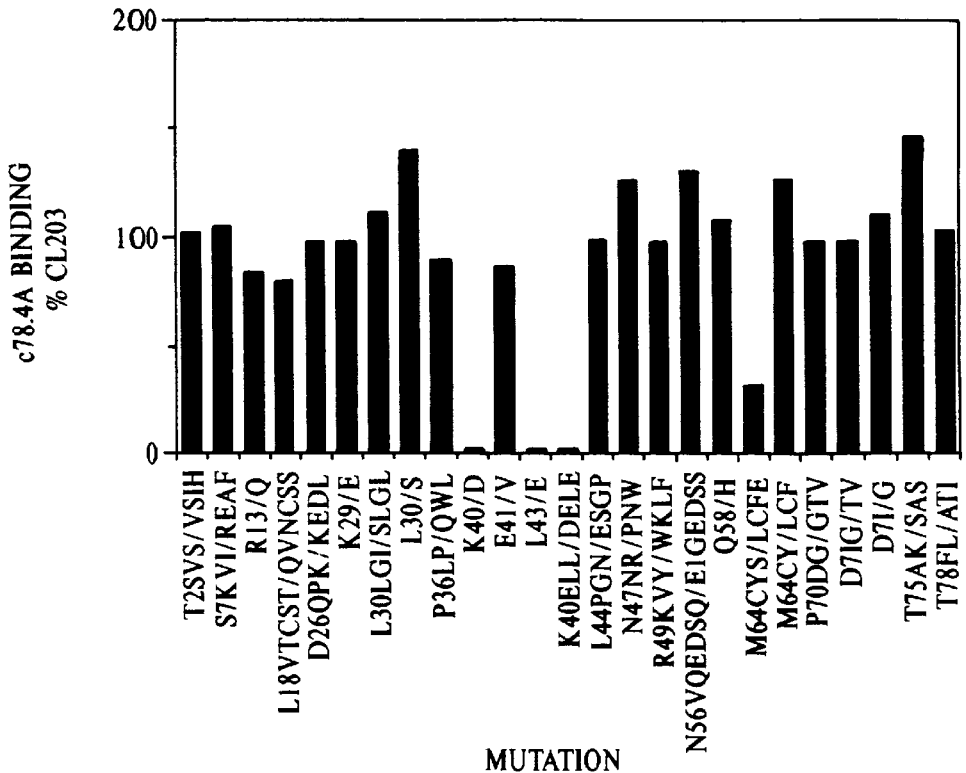
Figure 8D:
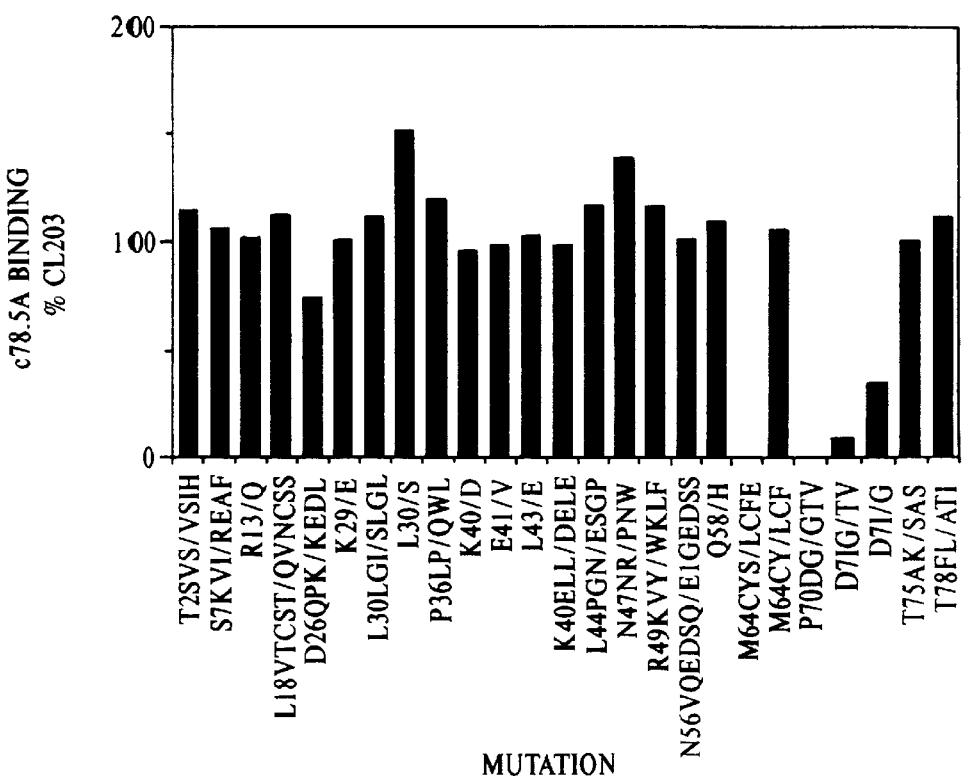

The domain II deglycosylation mutant was made by simultaneous priming with four mutangenic oligonucleotides designed to change Asn to Gln at each of the sites. In vitro transcription and translation of this mutant in the presence of dog pancreas microsomal membranes directs the synthesis of a core-glycosylated polypeptide of 63 kD, consistent with the absence of four sites of Asn-linked glycosylation (data not shown). The partially deglycosylated ICAM-1 molecule was expressed in COS cells which were tested for the ability to bind HRV-3 (FIG. 7). Essentially identical values were obtained for binding to wild-type and mutant receptors, indicating that the carbohydrate chains on domain II have no involvement in rhinovirus attachment. Lineberger, D. W., D. J. Graham, J. E. Tomassini, and R. J. Colonno, "Antibodies that block rhinovirus attachment map to domain I of the major group receptor", J. Virol. (1990) 64:2582–2587 concluded that glycosylation was involved in virus binding based on the lack of virus binding to receptor made in the presence of tunicamycin. A possible explanation for these apparently conflicting results is that glycosylation is required for the proper folding and transport of ICAM-1 to the cell surface. In support of this interpretation, we have observed that a soluble form of domains I and II fails to be secreted when all four glycosylation sites are deleted.

EXAMPLE 15

COS Cell Transfections

COS cell monolayers at 40% confluence in 150 cm$^2$ flasks were transfected with 5 μg of plasmid miniprep DNA by the DEAE dextran method [Kingston, R. E., "Introduction of DNA into mammalian cells", in Current Protocols in Molecular Biology, F. M. Ausubel, R. Brent, R. E. Kingston, D. D. Moore, J. G. Seidman, J. A. Smith, and K. Struhl, eds. (Greene Publishing Associates and John Wiley and Sons, New York, 1987), pp. 9.0.1–9.9.6].

EXAMPLE 16

Binding of Human/Mouse Chimeric tICAMs to anti-ICAM-1 Antibodies

Cells from Example 15 were analyzed 48 hours after transfection by flow cytometry on a FACSscan using monoclonal antibodies c78.4A, c78.5A and CL203 as previously described [McClelland, A., M. E. Kamarck, and F. H. Ruddle, "Molecular cloning of receptor genes by transfection," Meth. Enzymol. (1987) 147:280–291]. Purified CL203 antibody, which recognizes a site in the membrane-proximal part of the molecule [Staunton et al., Cell (1990) 61:243–254], was provided by S. Feronne (New York Medical College, Valhalla, N.Y.). All of the mutants bound CL203, with between 10% and 40% positive cells in each experiment. Monoclonal antibodies c78.4A and c78.5A were isolated following immunization of mice with HeLa cells by screening for inhibitory activity against rhinovirus infection as described in Example 2 above [Greve et al., Cell (1989) 56:839–847]. Antibody reactivity with each mutant was expressed as the percentage of cells staining with c78.4A or c78.5A compared to control staining with the CL203 antibody in the same transfection (FIG. 8). The percentage of ICAM-1-positive COS cells in these experiments varied from 11% to 48%. The murine L-cell line FT16.1 transfected with the mouse ICAM-1 CDNA and anti-mouse ICAM-1 antibody 3E5 were provided by Dr. A. Brian, UCSC.

Figure 9A:
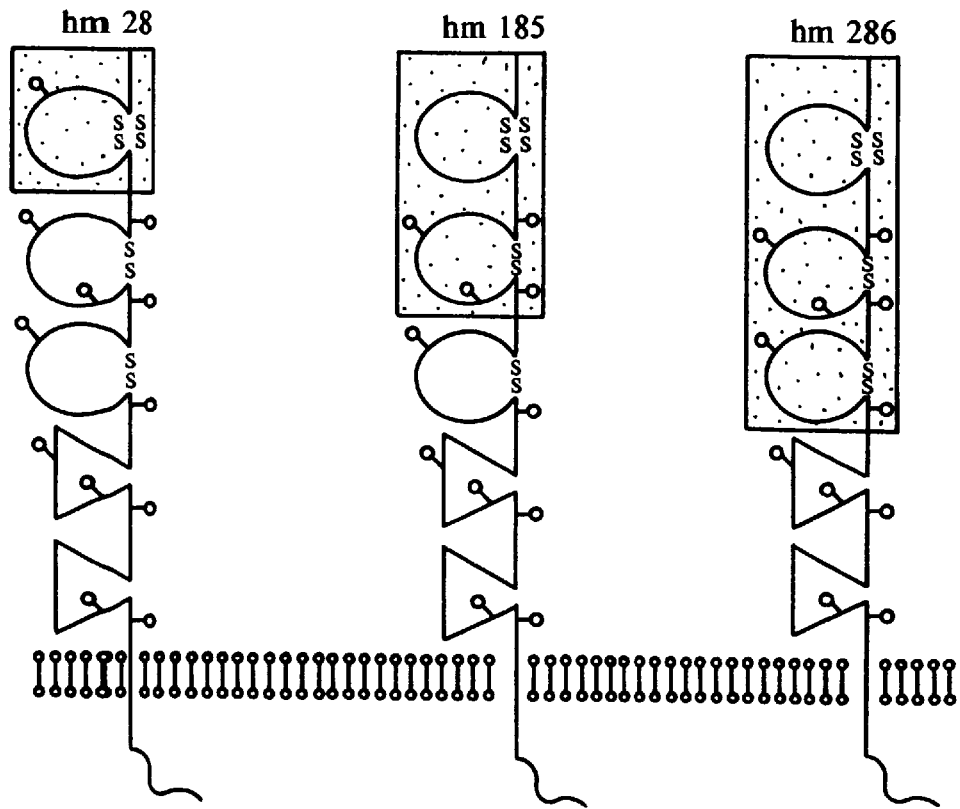
Figure 9B:
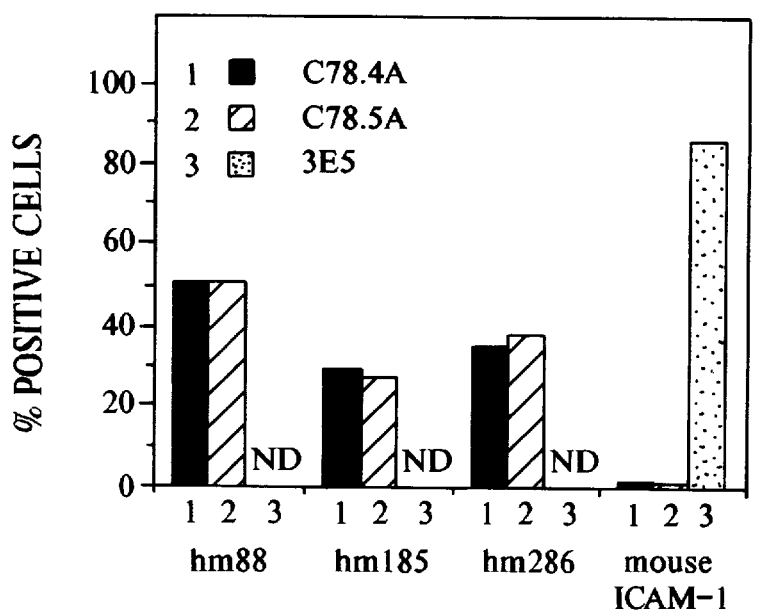

The chimeric molecules of Example 12 were expressed in COS cells as in Example 15 and analyzed for antibody reactivity by FACS with monoclonal antibodies c78.4A and c78.5A (FIG. 9B). Since neither antibody reacts with mouse ICAM-1, the binding of both antibodies to the hm88 chimera localizes the epitopes for c78.4A and c78.5A to domain I of ICAM-1 (FIG. 9B).

By replacing predicted beta strands or turns with blocks of corresponding murine sequence as in Example 13, we sought to avoid introducing changes which would alter the conformation of the domain. This approach was successful in that only one of 25 mutations simultaneously affected the binding of both monoclonal antibodies. Only one of the mutants, in which Met-Cys-Tyr-Ser [SEQ ID NO:22] at positions 64–67 were changed to Leu-Cys-Phe-Glu [SEQ ID NO:23], respectively, affected the binding of both antibodies, reducing c78.4A binding significantly and virtually eliminating c78.5A binding. This mutation introduces a negative charge within the F strand at residue 67 which is predicted to have its side chain pointing inward and therefore probably alters the overall conformation of domain I. In support of this interpretation, a mutant which Met-Cys-Tyr at positions 64–66 were changed to Leu-Cys-Phe, respectively, had no effect on the binding of either antibody. Since none of the other mutations disrupted both epitopes, any effects on antibody or virus binding are likely to be indicative of contacts in the area of the mutation, due either to local conformational changes or direct involvement of the altered residues.

Mutations which specifically eliminated binding of c78.4A were exclusively within the region predicted to comprise beta strand D on the four-strand side of the beta sandwich [Giranda et al., Proteins (1990) 7:227–233; Williams and Barclay, Ann. Rev. Immunol. (1988) 6:381–405], and were limited to residues 40 and 43. Thus changing Lys at position 40 to Asp, changing Leu at position 43 to Glu, or changing Lys-Glu-Leu-Leu [SEQ ID NO:13 ] at positions 40–43 to Asp-Glu-Leu-Glu [SEQ ID NO:15] completely eliminates c78.4A binding but still permits normal reaction with c78.5A. Residue Glu-41 which is conserved in the mouse protein does not appear to be involved in c78.4A recognition, since the change to Val had no effect. Beta strands are comprised of alternating inward-pointing hydrophobic amino acids and outward-pointing hydrophilic residues. Thus if residues 40 and 43 are part of a beta structure, their spacing dictates that only one of the two residues is oriented to the exterior of the domain. It is quite plausible that mutation of an inward-pointing residue could influence the local conformation in the region of antibody contact. Alternatively, residue 40 may form part of the loop preceding the D strand.

Mutations which affect the binding of c78.5A are located in the predicted loop between beta stands F and G at the N-terminal end of the domain. Single and double mutants at Asp-71 and Gly-72 reduce c78.5A binding significantly, while reactivity is completely eliminated by changing Pro-Asp-Gly at positions 70–72 to Gly-Thr-Val. A modest but reproducible effect on c78.5A binding is also seen when changing Asp-Gln-Pro-Lys [SEQ ID NO:4] at positions 26–29 to Lys-Glu-Asp-Leu [SEQ ID NO:13], which is predicted from the alignment to form the loop between beta stands B and C. Thus, the N-terminal loop region between strands F and G forms a major part of the c78.5A epitope, which to a lesser extent appears to involve the adjacent B to C loop.

The IgG fold structure places the B to C and F to G loops in relatively close proximity at the N-terminal end of the molecule (FIG. 7), consistent with antibody contact to both. The epitopes for c78.4A and c78.5A thus map to the D strand and FG loop respectively, with a small contribution to the c78.5A-epitope from residues in the BC loop. These mutations define a minimum area of potential contact between the antibody molecules and domain I since conserved residues and tolerated replacements involved in antibody binding would not be detected. Since the interface between antibody and protein antigen is 25 to 30 Å in diameter [Colman, P. M., "Structure of antibody-antigen complexes: implications for immune recognition," Adv. Immunol. (1988) 43:99–132], the mutations which affect binding are unlikely to define the entire contact surface, but do localize key residues of the epitopes. We have found that residues in beta strands D and G, and the F to G loop form a key part of the virus-binding site since mutations in these areas had the greatest effect on virus binding.

The effect of these antibodies on virus attachment could be due to direct masking of virus contact points on the ICAM-1 molecule or to steric effects preventing the binding site residues from penetrating the canyon, or a combination of both.

EXAMPLE 17

Binding of Human/Mouse Chimeric ICAMs to HRV

For virus-binding assays cells from one 150-cm$^2$ flask were detached with trypsin one day after transfection and replated in 6 wells of a 24-well microtiter plate to give a final cell density of approximately 5×10$^5$ cells per well. At 48 hours after transfection, virus binding assays were done using 20,000 cpm per well of sucrose gradient purified [$^{35}$S]-labelled HRV-3 prepared as described (Minor, P. D., "Growth, assay and purification of picornaviruses", in *Virology: A practical approach,* B. W. J. Mahy, ed.("Oxford, IRL Press, 1985), pp. 203–212). For each mutant, 3 wells were preincubated for 60 min at 37 C with 1 μg/ml of virus blocking antibodies c78.4A or c78.5A prior to addition of virus, and 3 wells received no antibody. Binding assays were performed with gentle rotation in a 5% $CO_2$ atmosphere at 37° C. for 2 hours in DMEM containing 2% serum and 10 mM HEPES pH 7.2. The monolayers were washed 3 times with PBS and then solubilized with 1% SDS for 20 min at 37° C. and cell-associated radioactivity determined by scintillation counting. Specific virus binding was determined by subtracting cell-associated counts in the presence of antibody from the values obtained in the absence of antibody. The percentage of input virus specifically bound in these experiments ranged from 16% to 41%. Each virus binding experiment included control binding to cells transfected with wild-type ICAM-1 and the CDM8 vector. Relative virus binding was then expressed as the percentage of virus binding to mutant versus wild-type ICAM-1 in the same transfection experiment. No adjustment was made for variations in expression since the level of ICAM-1 expressed in each experiment was sufficient to allow maximal virus binding.

Rhinovirus binding to transfected COS cell monolayers was tested in parallel with FACS analysis to confirm expression of the mutants. Virus binding to each of the three chimeric molecules of Example 12 was comparable to wild-type human ICAM-1 (FIG. 7), while cells expressing mouse ICAM-1 showed no specific binding. This result indicates that the region of human ICAM-1 which confers specificity for rhinovirus binding lies within the first 88 amino acids.

Figure 10:
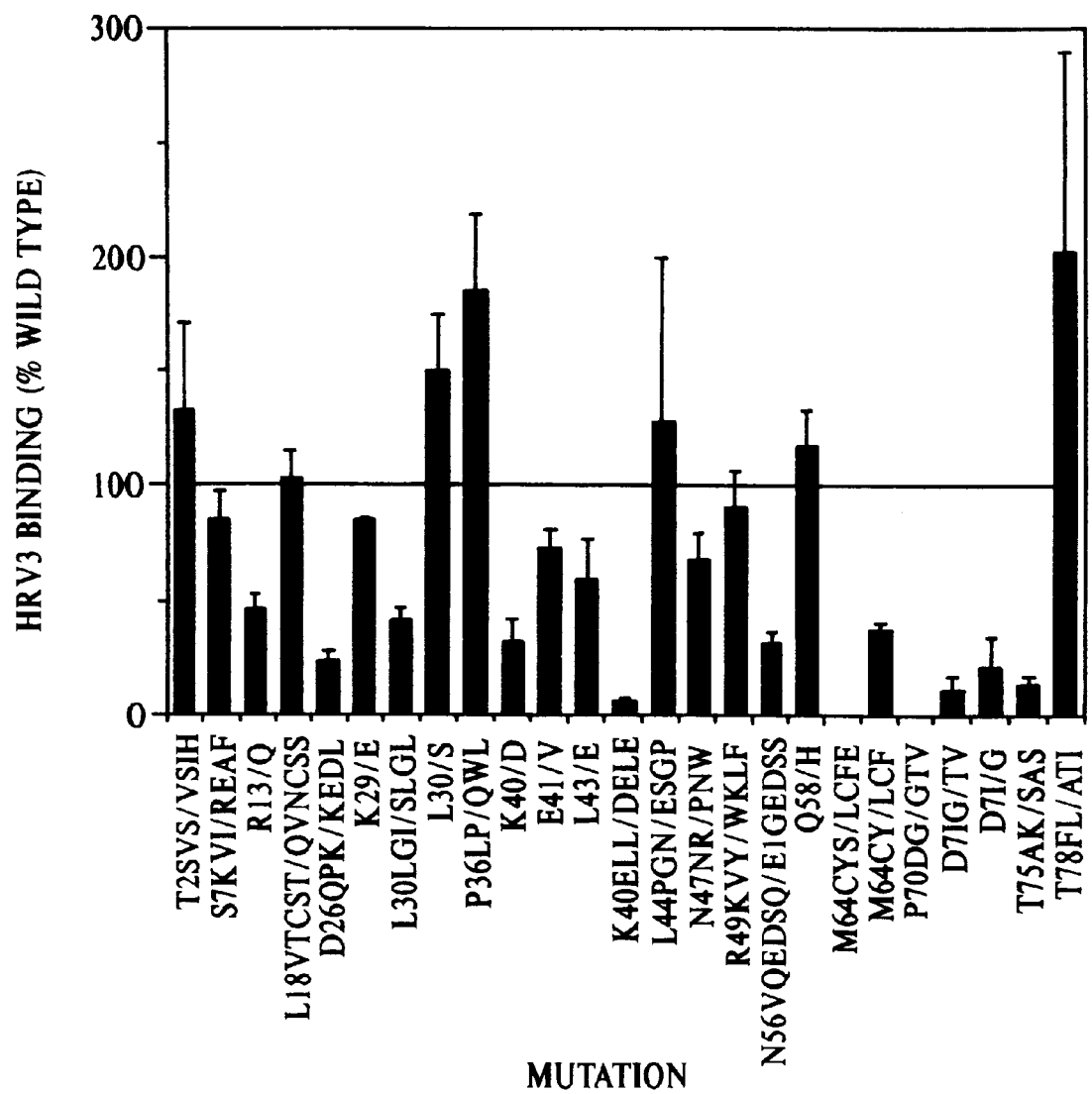

The results of [$^{35}$S]-labelled HRV-3 binding to COS cell monolayers transfected with each of the mutants is summarized in FIG. 10. Each experiment included FACS analysis of the level of expression and virus binding to wild-type ICAM-1 and CDM8 vector in control transfections. The level of virus binding to each of the mutants is expressed relative to virus binding to wild-type ICAM-1 in the same experiment and each value is the result of at least two determinations from separate transfection experiments. Strikingly, the mutations which produce the greatest reduction In rhinovirus binding correspond to mutations which also affect the binding of monoclonal antibodies c78.4A and c78.5A. Mutants in which Lys at position 40 was changed to Asp or Leu at position 43 was changed to Glu in the c78.4A binding site show a 3-fold and 2-fold reduction respectively, while the combined double mutant exhibits a ten-fold reduction. Mutants in the c78.5A binding site show reduced virus binding which correlate with the reduction in reactivity with the antibody. Changing Asp at position 71 to Gly reduces binding five-fold; changing Asp-Gly at position 71–72 to Thr-Val shows a ten-fold reduction; and changing Pro-Asp-Gly at positions 70–72 to Gly-Thr-Val, which eliminates c78.5A binding, also abolishes rhinovirus attachment. Mutation of residues 26–29 which are also implicated in c78.5A binding produces a four-fold reduction in binding. Changing Met-Cys-Tyr-Ser [SEQ ID NO:22] at positions 64–67 to Leu-Cys-Phe-Glu [SEQ ID NO:23], respectively, also completely eliminates virus binding, but as discussed above, probably induces a major conformational change which disrupts the virus binding site.

Of the mutants which reduce virus binding significantly but have no effect on antibody binding, several involve regions of the domain which are likely to be in close proximity to if not part of the antibody combining sites. These are mutants in which Leu-Leu-Gly-Ile [SEQ ID NO:5] at positions 30–33 in the C strand are changed to Ser-Leu-Gly-Leu [SEQ ID NO:14], respectively; Met-Cys-Tyr at positions 64–66 in the F strand are changed to Leu-Cys-Phe, respectively; and Thr-Ala-Lys at positions 75–77 at the N-terminal end of the G strand are changed to Ser-Ala-Ser, respectively. Only two mutants which reduce virus binding are predicted to lie at the C-terminal end of the domain, in the loops between A and B, and E and F strands.

By transferring intact domains of human ICAM-1 to the mouse molecule, we have shown that the epitopes for both virus blocking monoclonal antibodies c78.4A and c78.5A reside within the first domain, and that human domain I alone is capable of converting murine ICAM-1 to rhinovirus binding. This result demonstrates that rhinovirus binding specificity is imparted by the first 88 residues of human ICAM-1, although it does not rule out the involvement of other domains in virus binding. Our experience with the expression of soluble truncated forms of ICAM-1 and the results of Staunton et al., Cell (1990) 61:243–254, suggest that the first two domains of ICAM-1 are conformationally linked. If this is the case however, murine domain II can substitute for the human domain II and allow virus binding.

The virus binding results suggest that the antibodies recognize groups of residues in domain I which are directly involved in contact with the virus, since the greatest effects on binding were caused by mutations in these areas (FIG. 10). In addition, several other mutations which affected virus binding are predicted to be adjacent to the epitope locations. These results indicate that an extensive area of the surface of ICAM-1 domain I is involved in contact with rhinoviruses. This area includes the N-terminal end of the molecule and beta strands D and G on the four and three strand faces of the domain respectively.

A model of ICAM-1 domain I was docked into the rhinovirus canyon in an attempt to predict possible sites of contact [Giranda et al., Proteins (1990) 7:227–233]. The shape and dimensions of the model allow the N-terminal half of the domain to fit into the canyon and do not constrain its orientation about the long axis. A proposed orientation was made based on maximizing charged and polar interactions between virus and receptor residues. This model predicts interaction between residues in the N-terminal loop regions of domain I as well as in the D and G beta strands. Our mutagenesis data support the general features of this model in that the areas of proposed interaction are those which we find are most important for virus binding. However several of the specific ICAM-1 residues proposed to form salt bridges with canyon residues were altered in some of our mutants which had no effect on virus binding. Two mutations which weakly affected virus binding are located towards the C-terminal end of domain I, suggesting that this part of the domain may interact with exposed parts of the virus surface on the canyon rim.

While the present invention has been described in terms of specific methods and compositions, it is understood that variation and modifications will occur to those skilled in the art upon consideration of the present invention.

For example, it is anticipated that smaller protein fragments and peptides derived from ICAM-1 that still contain the virus-binding site would also be effective.

Further, it is anticipated that the general method of the invention of preparing soluble protein forms from insoluble, normally membrane bound receptor proteins can be used to prepare soluble multimeric forms of other receptor proteins useful for binding to and decreasing infectivity of viruses other than those that bind to the "major group" receptor. Such other viruses include Herpes simplex and Epstein-Barr viruses.

Accordingly, it is intended in the appended claims to cover all such equivalent variations which come within the scope of the invention as claimed, and consequently only such limitations as appear in the appended claims should be placed thereon.

We claim:

1. An antiviral analog of ICAM-1 comprising domain I wherein amino acid residues Thr-2/Ser-3Val-4/Ser-5 (SEQ ID NO: 16) have been changed to Val- 2/Ser-3/Ile-4/His-5 (SEQ ID NO: 7).

2. An antiviral analog of ICAM-1 comprising domain I wherein amino acid residue Leu-30 has been changed to Ser-30.

3. An antiviral analog of ICAM-1 comprising domain I in which amino acid residues Pro-36/Leu-37/Pro-38 have been changed to Gln-36/Trp-37/Leu-38.

4. (amended) An antiviral analog of ICAM-1 comprising domain I in which amino acid residues Leu44/Pro45/Gly46/Asn-47 (SEQ ID NO: 16 have been changed to Glu 44/Ser45/Gly46/Pro-47 (SEQ ID NO: 17).

5. An antiviral analog of ICAM-1 comprising domain I in which amino acid residue Gln-58 has been changed to His-58.

6. An antiviral analog of ICAM-1 comprising domain I in which amino acid residues Thr-78/Phe-79/Leu-80 have been changed to Ala-78/Thr-79/Ile-80.

7. A method for reducing the infection by human rhinovirus (HRV) of host cells susceptible to infection by HRV, comprising contacting the virus under conditions favorable for binding with the antiviral analog of ICAM-1 of claim 3.

8. A method for reducing the infection by human rhinovirus (HRV) of host cells susceptible to infection by HRV, comprising contacting the virus under conditions favorable for binding with the antiviral analog of ICAM-1 of claim 2.

9. A method for reducing the infection by human rhinovirus (HRV) of host cells susceptible to infection by HRV, comprising contacting the virus under conditions favorable for binding with the antiviral analog of ICAM-1 of claim 3.

10. A method for reducing the infection by human rhinovirus (HRV) of host cells susceptible to infection by HRV, comprising contacting the virus under conditions favorable for binding with the antiviral analog of ICAM-1 of claim 4.

11. A method for reducing the infection by human rhinovirus (HRV) of host cells susceptible to infection by HRV, comprising contacting the virus under conditions favorable for binding with the antiviral analog of ICAM-1 of claim 5.

12. A method for reducing the infection by human rhinovirus (HRV) of host cells susceptible to infection by HRV, comprising contacting the virus under conditions favorable for binding with the antiviral analog of ICAM-1 of claim 6.

* * * * *